United States Patent [19]

Franson et al.

[11] Patent Number: 6,020,510
[45] Date of Patent: Feb. 1, 2000

[54] CYTOPROTECTIVE COMPOUNDS

[75] Inventors: Richard C. Franson, Richmond; Raphael M. Ottenbrite, Midlothian, both of Va.

[73] Assignee: Virginia Commonwealth University, Richmond, Va.

[21] Appl. No.: 09/017,511

[22] Filed: Feb. 2, 1998

Related U.S. Application Data

[63] Continuation of application No. 08/632,030, Apr. 15, 1996, Pat. No. 5,859,271.

[51] Int. Cl.[7] ................................................. C07C 69/58
[52] U.S. Cl. ............................ 554/224; 554/223; 554/227
[58] Field of Search .................................... 554/224, 227, 554/223

[56] References Cited

U.S. PATENT DOCUMENTS

| | | | |
|---|---|---|---|
| 4,701,469 | 10/1987 | Mendy et al. | 514/547 |
| 4,927,658 | 5/1990 | Klemann et al. | 426/611 |
| 5,659,049 | 8/1997 | Franson et al. | 548/400 |
| 5,659,055 | 8/1997 | Franson et al. | 554/88 |

FOREIGN PATENT DOCUMENTS

| | | |
|---|---|---|
| 653709 | 2/1995 | Australia . |
| 2005750 | 8/1990 | Canada . |
| 1322200 | 9/1993 | Canada . |
| 0 443 313 A1 | 8/1991 | European Pat. Off. . |
| 2 279 948 | 1/1995 | United Kingdom . |
| 88/06445 | 9/1988 | WIPO . |
| WO 91/03512 | 3/1991 | WIPO . |

OTHER PUBLICATIONS

Bhatnagar, et al. "Synthetic Ester Lubricants: Pt. I–Synthesis and Properties of 2,2–Dialkyl–1, 3–Propanediol Esters", *J. Indian Chem. Soc.*, vol. LVIII, pp. 594–596 (1981).

Brem, et al., "Interstitial Chemotherapy with Drug Polymer Implants for the Treatment of Recurrent Gliomas", *J. Neurosurg.*, vol. 74, pp. 441–446 (1991).

Clapp, et al., "Phospholipase $A_2$–induced neurotoxicity in vitro and in vivo in rats", *Brain Research*, vol. 693, pp. 101–111 (1995).

Clay, et al., "Structural Characterization of Lipids Which Develop During Blood Storage and Prime Neutrophils Via Platelet Activating Factor Receptors", *Third International Congress: Eicosanoids & Other Bioactive Lipids in Cancer, Inflammation & Radiation Repair*, Abstract #192.

Franson, et al., "Mechanism(s) of Cytoprotective and Anti–Inflammatory Activity of $PGB_1$ Oligomers: $PGB_x$ has Potent Anti–Phispholipase $A_2$, and Anti–Oxidant Activity", *Prostaglandins, Leukotrienes and Essential Fatty Acids*, vol. 43, pp. 63–70 (1991).

Goshray, S. et al., "Enzymatic Preparation of Ricinoleic Acid Esters of Long–Chain Monohydric Alcohols and Properties of the Esters", *JAOCS*, vol. 69, No. 1, pp. 85–88 (1992).

O'Brien, David F., et al., "Preparation and characterization of polymerized liposomes", *Ann. N.Y. Acad. Sci.*, No. 446, pp. 282–95, (1985).

Stephenson, et al., "Cytosolic Phospholipase $A_2$ ($cPLA_2$) Immunoreactivity is Elevated in Alzheimer's Disease Brain", *Neurobiology of Disease*, vol. 3, pp. 51–63, (1996).

Teupel, et al., "Analysis of ricinoleic acid monoglycerides by column chromatography and nuclear magnetic resonance spectroscopy", *Tenside*, vol. 5 (9–10), pp. 275–278 (1968).

Vitsina, et al., "Cooling Liquid Lubricant for Cold Processing of Metals", *Chemical Abstracts*, vol. 068, No. 12, Abstract No. 052458, p. 5097 (1968) (Abstract Only).

Watanabe, et al. "New Additives Derived from Fatty Acids for Water–Based Cutting Fluids", *Journal of the American Oil Chemists' Society*, vol. 62, No. 1, pp. 125–127 (1985).

Yonese, et al., "Detection for Heating Products of Ricinoleic Acid and Separation of Polyricinoleic Acids", *Chemical Abstracts*, vol. 95, No. 14, Abstract No. 117410, p. 105 (1981) (Abstract Only).

*Primary Examiner*—James H. Reamer
*Attorney, Agent, or Firm*—Jones & Askew LLP

[57] ABSTRACT

The present invention provides compositions and methods for protecting cells from injury due to intrinsic membrane lysis, oxidation and/or invasion by destructive agents. Even more particularly, the present invention provides compositions and methods for treating or prophylactically inhibiting phospholipase mediated injury, injury due to oxidation, and inflammation. In a very specific sense, this invention provides compositions and methods of making these compositions that are inhibitors of phospholipase.

31 Claims, No Drawings

CYTOPROTECTIVE COMPOUNDS

This application is a continuation of application Ser. No. 08/632,030 now U.S. Pat. No. 5,859,271, filed Apr. 15, 1996, entitled "Cytoprotective Compounds".

FIELD OF THE PRESENT INVENTION

The present invention relates to compositions and methods for protecting mammalian cells from injury due to intrinsic membrane lysis, oxidation and/or invasion by destructive agents. In particular the present invention relates to compositions and methods for treating against and/or prophylactically inhibiting the injury causation. Even more particularly, the present invention relates to bioactive agents and the use thereof for treating or prophylactically inhibiting phospholipase mediated injury, injury due to oxidation, and inflammation. In a specific sense the present invention provides agents for preventing and/or treating inflammation and cell destruction in mammalian tissue and for protection and preservation of biologic material derived from animals, humans and plants such as food and tissue samples. In a very specific sense, this invention provides compositions that are inhibitors of phospholipase and methods of making these compositions.

BACKGROUND OF THE INVENTION

The base structure of all living organisms is the cell which is structurally defined by its membranous lipoprotein envelope. The membranous network that holds the cell together maintains the ionic balance and provides the receptors for hormones and neurotransmitters that enable a cell to interact with its environment. This is pertinent to interaction with neighboring cells which enable isolated cells, tissues, or whole organisms to survive as both independent units and as participants in cellular interactions, in vitro and in vivo.

External factors which govern cell function, renewal, reproduction and death act via their effects on the phospholipid bilayer and proteins of the cell membrane. This controls the receptor-mediated signals and ionic fluxes which govern cell responsiveness and survival. Damage to the cell membrane with particular emphasis on lipid peroxidation, membrane oxidation and the action of phospholipases, affects resistance to injury, repair and host responses to environmental change and ionic and osmotic integrity.

Pathological events in a host under clinical circumstances can result in cellular insult, leading to loss of membrane integrity. The events are mediated by factors which digest and destroy cell membrane and propagate an injury by producing a cascade of cell membrane changes. By interfering with the cascade of external and internal events involving membrane integrity and toxic changes which lead to cell death, injury can be prevented, modified or reversed. This has been a major role of anti-inflammatory agents in the past.

The most important presently used clinically effective anti-inflammatory drugs include the corticosteroids and the non-steroidal anti-inflammatory drugs (NSAIDs). Corticosteroids inhibit the activity of cell phospholipases among other actions. NSAIDs inhibit the metabolism by cyclooxygenase of arachidonic acid released by phospholipases. These drugs act to control inflammation and to minimize cell injury by regulating the breakdown of phospholipids. These drugs also affect the action of the products of phospholipid breakdown leading to the formation of prostaglandins and leukotrienes which are produced in increased quantities in inflammation and promote cell dysfunction and injury.

In addition, cellular and extracellular phospholipases may be activated by the generation of oxygen free radicals. This can establish a damaging cycle as phospholipase activation can release free radicals which, in turn, activate more phospholipases. In this regard, free radicals are produced from the fatty acids which are released by the action of phospholipases and then converted to prostaglandins and leukotrienes by cyclooxygenase and lipoxygenase enzymes with oxygen free radical production as a by product. Fatty acids and free radicals are known to be prime mediators in the cascade of reactions that result in membrane injury, cell death and inflammation. Phospholipase $A_2$ ($PLA_2$), a key enzyme in the metabolism of phospholipid, can promote fatty acid release. $PLA_2$ may be activated by a variety of factors involving hormonal, neural, metabolic, or immunologic pathways.

One of the hallmarks of inflammation and cell injury is the breakdown of cellular membrane phospholipid. Phospholipids are the major structural building blocks of the cell membrane; they give rise to the barrier-structural and functional properties of membranes and their integrity is crucial to normal cell responsiveness and function. Phospholipid changes in cell membrane integrity, particularly changes in fatty acids at the 2 position, alter the fluidity of cell membranes, cell receptor function and the availability of cellular contents to the external environment. The breakdown of phospholipid membranes results in lysis of cells, produces holes in the cell membrane, affects ion channels and membrane receptors which destroy cellular integrity and functional responses.

During inflammation, phospholipases, from whatever source, that are normally under the control of natural suppressor systems, are activated to degrade membrane phospholipid which, in turn, generates oxygen free radicals. $PLA_2$ is a key enzyme which is activated in inflammation to metabolize substrate phospholipids and release free fatty acids. These fatty acids (i.e., arachidonate) released by $PLA_2$ are converted to potent biologically active metabolites, lysophospholipids, prostaglandins, and leukotrienes. These are themselves substrates for other enzymes leading to the production of thromboxanes, platelet activating factor and other substances, with the concomitant generation of oxygen free radicals.

Phospholipases, particularly $PLA_2$, as membrane targeted enzymes, play an important role since expression of their activity results in further production of inflammatory mediators leading to membrane injury which propagates damage within the cell itself or to adjacent tissue. Thus, the spread of injury from the initial site to contiguous or distant sites can be promoted by the activation and/or release of $PLA_2$.

In addition to the intrinsic membrane-related tissue breakdown via the activation of $PLA_2$, phospholipases, and particularly $PLA_2$, are part of the normal defense system of the body. $PLA_2$ is found in human white blood cells (WBCs). WBCs play a role in resisting infection, but when these cells are mobilized to ward off injury and infection, $PLA_2$ is released from adherent and circulating WBCs and produces local tissue activation which can increase the extent of initial injury. In addition, WBCs adhere to blood vessel walls where they release enzymes such as $PLA_2$. WBCs also generate free radicals such as superoxide, in large quantities, and thus promote damage to the vascular endothelium, lung alveoli or to tissue sites contiguous with WBC infiltration or concentration. Where inflammation is found, WBCs are usually present in abundance and the WBCs adhere to vascular endothelium, with subsequent release and activation of $PLA_2$ resulting in damage to vascular integrity during shock and ischemia. Thus, in spite of being a prime defense system of the body against infection, WBCs can also damage the body by propagating injury and inflammation.

A classical description of inflammation is redness and swelling with heat and pain. Inflammation has been defined as the reaction of irritated and damaged tissues which still retain vitality. Inflammation is a process which, at one level, can proceed to cell death, tissue necrosis and scarring. At another level, inflammation can be resolved with a return to normalcy and no apparent injury or with minimal changes, i.e., pigmentation, fibrosis or tissue thickening with collagen formation related to healing and scarring.

Microscopically, inflammation has been described as: (1) atony of the muscle coat of the blood vessel wall; (2) endothelial adherence of inflammatory cells followed by migration of these cells from the vascular space into tissue.

The events described above are often mediated by phospholipase activation, followed by fatty acid release and the formation of free radicals. Cytokines, secreted by immune cells, induce $PLA_2$ secretion by their actions on a variety of cells. Interleukin-6 stimulates hepatocytes to increase $PLA_2$ secretion many-fold. Interleukin-1 and tumor necrosis factor induce $PLA_2$ secretion by endothelial cells and by chondrocytes. Thus, immune cell products directly stimulate the hydrolysis of membrane phospholipids and production of arachidonic acid metabolites by a variety of target cells, amplifying the inflammatory response.

Alternatively, increased phospholipase activity can relate to exogenous enzyme released from infecting pathologic organisms such as viruses, bacteria, Rickettsia, protozoa, and fungi. These pathogens often possess phospholipases as factors intrinsic to their infectious activity. In the case of *Naegleria fowleri*, a pathogenic amoeba with affinity for the brain, destruction of brain membranes induced by phospholipases secreted by Naegleria can occur at sites in the brain distant from where the organism is localized. In another example toxoplasma cannot enter the host cell if its $PLA_2$ enzyme is inhibited by a specific drug. What is needed to treat certain infections, particularly intracellular pathogens, is an effective $PLA_2$ inhibitor. Such an effective $PLA_2$ inhibitor is particularly needed in cases of protozoal infections for which there are few effective antibiotics.

$PLA_2$ is also one of the major toxic components of snake venom. Bites of certain snakes inject venom containing $PLA_2$ into the wound, causing toxic and inflammatory responses which may be lethal. What is needed are inhibitors of $PLA_2$ which may be administered to recipients of snake bites and bites of other animals.

Pathologic effects of phospholipases may be local, regional or systemic. These pathologic effects are governed by the phospholipase enzyme released, the level of albumin, natural inhibitors of enzyme action, and factors of diffusion, circulation and tissue vulnerability based on intrinsic inhibitors or the susceptibility of previously damaged or oxidized membranes or proteins to phospholipase action.

Inflammation is associated with trauma, infection and host defense reactions related to direct bacterial or virus killing by the associated immune responses. In general, immune responses can be both beneficial, protective or tissue damaging as can be seen in their role to promote resistance to infection or cure of infection. Alternatively, immune responses may produce autoimmune phenomena that result in allergy, i.e., asthma, urticaria, in graft versus host disease, in glomerular nephritis, in rheumatic fever, or in lupus and rheumatoid arthritis.

In regard to the current treatment of inflammation, corticosteroids are effective anti-inflammatory agents, but must be used cautiously because they are powerful immunosuppressants and inhibitors of fibroblastic activity necessary for wound healing and bone repair. In addition, corticosteroids have powerful hormonal activities and their toxic side effects involve interference with wound repair and bone matrix formation, sodium retention, potassium loss, bone demineralization, decreased resistance to infection, and diabetes. Corticosteroids also have effects on steroid formation, cataracts, blood pressure, protein utilization, fat distribution, hair growth and body habitus. Alternatively, the clinically active NSAIDs, such as aspirin, indomethacin, ibuprofen, etc., work by inhibiting the conversion of free fatty acids to prostaglandins. The side effects of NSAIDs include gastric ulceration, kidney dysfunction and Reye's Syndrome. Metabolites of prostaglandin can be either damaging or protective to cells depending on the structure of the prostaglandin produced or utilized pharmacologically and the route of administration, cell or tissue effected.

As discussed previously, in conjunction with fatty acid release, leukotrienes are generated as part of phospholipid cell membrane mediated injury produced by phospholipase activation. These leukotrienes produced from membrane phospholipid breakdown damage tissue through direct toxic action, effects on ionic channels, and associated free radical formation. Leukotrienes also damage tissue by indirect effects on vascular smooth muscle or on the vascular endothelial lining via effects on platelets, WBCs, or endothelial cells, or secondarily through effects on constriction of smooth muscle. Leukotrienes are responsible for smooth muscle constriction leading to bronchospasm and the asthmatic attacks seen in allergy or infectious asthma. Thus, there is an ongoing search for leukotriene inhibitors for clinical application in the treatment of allergy, asthma and tissue injury and inflammation.

Because the phospholipase-activated biochemical pathway for the formation of prostaglandins and leukotrienes derived from free fatty acids is branched, inhibition of one branch of this pathway, as with NSAIDs, can create an imbalance in these reactive metabolites. This imbalance may actually aggravate inflammation and promote cell injury as evidenced by the gastric ulcerative side effects of NSAIDs.

Due to these adverse effects of both steroids and NSAIDs, there is great clinical interest in identifying phospholipase inhibiting agents that do not have steroidal or NSAID side effects, but like corticosteroids modulate the first step leading to the production of injurious metabolites, fatty acids and free radicals.

Free radicals, produced by white blood cells, tissue injury or metabolic processes, are highly reactive chemical species which, in the case of tissue injury, are most often derived from respiratory oxygen. Oxygen, while necessary for energetics of life, is also a toxin which, as the chemically related superoxide, or as peroxides, can damage tissue instead of supporting it. Free radicals derived from oxygen are critical to damage produced by radiation, inflammation, reperfusion tissue injury or through excess oxygen inhalation or exposure. Free radicals are used by white blood cells to destroy infecting organisms, but can, under circumstances of shock, infection and ischemia, damage or destroy the tissue they were meant to protect. Free radicals, induced by radiation, oxygen exposure, chemical agents (i.e., alkylating agents, dioxin, paraquat) or white blood cell reactions may damage tissue or be involved in mutational changes associated with aging, radiation or chemotherapy injury, the development of cancer, and hyperimmune proliferative disease such as rheumatoid arthritis. In addition, these reactive chemical species can, through oxidation of proteins, enhance the vulnerability of proteins to protease digestion.

The exact pathologic mechanisms of many skin inflammations, such as atopic dermatitis, are not clear, but probably involve inflammatory cells which can secrete or respond to $PLA_2$. Allergic diseases involve tissue mast cells, which can be primed or triggered by $PLA_2$ for the release of their inflammatory granule contents, such as histamine. These cells also release additional $PLA_2$. What is needed are inhibitors of PLA2 that adequately penetrate skin after topical application and possess prolonged anti-$PLA_2$ activity.

Previous published studies have demonstrated high levels of a proinflammatory $PLA_2$ in human herniated vertebral discs. The isolated enzyme is toxic to dorsal root ganglion cells in culture and excised sciatic nerve. While not wanting to be bound by this statement, it is believed that $PLA_2$ may mediate inflammation and nerve tissue damage in spinal cord injury and in sciatic nerve inflammation and may also mediate a variety of neurological inflammatory conditions. Recently, Stephenson et al., (Neurobiology of Disease 3:51–63 (1996) have observed elevated cytosolic $PLA_2$ activity in brains with Alzheimer's disease.

$PLA_2$ also has the capability to induce severe, delayed neurotoxicity syndrome, including extensive cortical and subcortical injury to forebrain neurons and fiber pathways, when injected intracerebroventricularly as described by Clapp et al. (Brain Research 693:101–111,1995) the entirety of which is incorporated herein by reference. We have also observed that preparations of $PLA_2$ and homogenates of human vertebral disks containing extracts of the nucleus pulposus are inflammatory when injected into the mouse paw and induce edema. Edema induced by human disk homogenate is maximal between 1–3 hrs and remains so for at least 6 hrs. These results support the hypothesis that leakage of nucleus pulposus from a herniated disk may promote inflammation in human disk disease. Accordingly, what is needed are inhibitors of $PLA_2$ mediated inflammatory processes. Such inhibitors should alleviate the inflammation and resultant pain and discomfort associated with disk disease and other neurological inflammatory conditions.

Tissues that are excised from animals for subsequent transplantation into recipients often display damage following transplantation during reperfusion of ischemic tissue. Both ischemia and reperfusion increase $PLA_2$ activity and release leading to inflammatory processes with marked activation of the vascular endothelium. These processes decrease the probability of successful transplantation thereby increasing the incidence of rejection and the need for additional immunosuppressive therapy. Such problems greatly increase morbidity and mortality, increase the costs of treatment and insurance, and result in lost time at work. What is needed are drugs that will inhibit $PLA_2$ activity and enhance tissue preservation before transplantation thereby decreasing ischemia reperfusion injury.

Infections caused by parasites constitute a major public health problem throughout the world for humans and animals, annually resulting in significant incidence of disease, suffering and death. Parasites such as those that cause malaria and other protozoal parasites of animals and humans are especially troublesome. We have found that the $PLA_2$ inhibitor, quinacrine (mepacrine), significantly reduced molting of larval forms of an animal filarid. What is needed are new compounds that effectively inhibit $PLA_2$ activity for application to parasites such as those causing malaria and other protozoal parasites injurious to animals and humans.

A previous study by Clay et al. (Third International Congress: Eicosanoids & Other Bioactive Lipids in Cancer, Inflammation, & Radiation Repair, Abstract #162) reported that the product of $PLA_2$ activation, 1-acyl lysophospholipid, which affects membrane fluidity, accumulates in stored blood and may be taken up by white blood cells (WBCs) and used to make platelet activating factor (PAF) thereby "priming" WBCs during storage and promoting injury during subsequent transfusion. It has been suggested that increased $PLA_2$ activity may perturb cells in storage. What is needed are compounds that protect blood cells and other cells during storage so that these cells will not cause problems when utilized.

Accordingly, what is needed are compounds and methods of using these compounds which provide protection against the deleterious effects of $PLA_2$ activation. These compounds should be capable of inhibiting $PLA_2$, thereby decreasing the $PLA_2$ metabolites which are substrates for the cyclooxygenase, 5-lipoxygenase, 12-lipoxygenase, and other enzymatic pathways which lead to formation of cyclic endooperoxides, prostaglandins (such as prostacyclin and thromboxane), leukotrienes, and platelet activating factor. These compounds should decrease inflammatory processes and free radical production in a variety of tissues and cells. They should be capable of being administered in vivo (topically, orally, by injection and through other means), ex vivo and in vitro and should also exhibit low or no toxicity. These compounds should display different solubilities in lipid and aqueous systems depending on the mode of application and the desired target.

SUMMARY OF THE INVENTION

The present invention provides both lipid and/or water soluble compounds that are $PLA_2$ inhibitors having antioxidant properties and/or antiinflammatory properties. This invention provides bioactive compounds which are oligomers (dimers, trimers and tetramers, etc.) of fatty moieties that inhibit $PLA_2$ activity. The terms dimer, trimer, tetramer and pentamer as used throughout the present description define the number of fatty moieties present in the particular molecule. That is to say a dimer has two fatty moieties, a trimer has three, a tetramer has four, a pentamer has five, etc. The compounds of the present invention possess at least one double bond to enhance their anti-inflammatory and cytoprotective or tissue protective effects.

The compounds of the present invention may be used for treating or prophylactically inhibiting phospholipase mediated injury and/or injury due to oxidation. In a specific sense, the present invention provides agents for preventing and/or treating inflammation and cell destruction in mammalian tissue and for protection and preservation of biologic material such as cells, tissues, organs and fluids obtained from animals and humans. The present invention also provides agents for protection and preservation of food obtained from animals and plants, and for cellulose products and wood products obtained from plants. The compounds of the present invention protect phospholipid cell membranes, and proteins from the effects of oxidative injury or aging. These compounds of the present invention also inhibit free radical reactions and thereby stabilize proteins for maintenance of biologic half-life, anti-coagulant activity, and food preservation.

More specifically, the present invention provides pharmacologically active, anti-phospholipase compounds. These compounds are soluble and/or dispersible in a suitable carrier. The compounds may exist as oligomers such as dimers, trimers, tetramers etc., or as combinations thereof. In accordance with the present invention, the compounds have at least two fatty moieties and contain at least one unsaturated double bond. Each fatty moiety may take a variety of forms, may possess the same or different functional groups, may be a different length. In one preferred form, the compounds of the present invention may have an acid group or any salt form thereof. The compounds of the present invention may also be present in ionized form.

Accordingly, an object of the present invention is to provide compositions that inhibit the activity of the enzyme $PLA_2$.

It is a related object of the present invention to decrease levels of products of the enzymes cyclooxygenase, 5-lipoxygenase, 12-lipoxygenase, prostacyclin oxycyclase, thromboxane synthase, and prostaglandin isomerase pathways by inhibiting the activity of $PLA_2$.

Another object of the present invention is to provide methods of synthesizing these compositions that inhibit the activity of $PLA_2$.

It is also an object of the present invention to provide methods of treating conditions associated with PLA$_2$ activity.

Yet another object of the present invention is to provide a composition and treatment for oxidative and free radical damage to cells, tissues and organs in vitro and in vivo.

Another object of the present invention is to provide methods of applying an effective amount of the compositions to treat inflammation.

Another object of the present invention is to provide a composition and treatment for inflammatory processes.

It is also an object of the present invention to provide oral and topical treatments for arthritis with the compositions of the present invention.

Yet another object of the present invention is to provide treatments for pain using the composition of the present invention.

Another object of the present invention is to provide oral and topical treatments comprising administration of an effective amount of the compositions of the present invention, for a variety of conditions, such conditions including, but not limited to, the following: reflex sympathetic dystrophy; inflammation of the central and peripheral nervous system, diseases related to inflammation of the nervous system including, but not limited to, Alzheimer's disease, inflammation of spinal nerves, autonomic nerves and cranial nerves; inflammatory radiculopathy; back pain including low back pain; myo-fascial pain syndromes; inflammation of the connective tissues including meninges, inflamed and diseased facet Joints, herniated disks, diseased disks, torn and injured annulus fibrosis, diseases of the joints, ligaments, cartilage and synovial membranes; mastocytosis; shock including septic shock, anaphylactic shock, anaphylactic shock resulting from radiocontrast administration, and shock resulting from bacterial infections; bacterial infections; uremia; autoimmune disorders; parasitic infections including, but not limited to, malaria; inflammation including allergic inflammation; skin inflammation, itching, and other dermatologic disorders due to allergic reactions, dry skin, erythema, solar, nuclear and other forms of radiation, windburn, acne, psoriasis, eczema, reactions to chemicals and toxins, contact dermatitis, and reactions to plants including, but not limited to, poison ivy, poison oak, poison sumac; bites of insects including, but not limited to, mosquitos, fire ants, chiggers, ticks, bees, spiders, fleas and flies; bites of reptiles, especially venomous reptiles, amphibians, and other animals; contact with various animals with venom on their skin such as poisonous frogs; pruritis associated with local dermatologic or systemic disease; prevention of tissue ischemia including tissue in vivo and tissue destined for transplantation, prevention of ischemia-reperfusion injury, prevention of ischemia-reperfusion injury in the setting of resuscitation from hypovolemic shock, renal ischemia, myocardial infarction, angina, and cardiac ischemia; endothelial inflammation, cardiotoxicity associated with administration of anti-cancer compositions, inhibition of coronary or cerebral restenosis following angioplastic or other vascular procedures, inhibition of platelet activity, especially in vessels following various procedures such as angioplasty and after insertion of catheters, shunts and other devices, inhibition of thrombin-activated platelet aggregation; pulmonary diseases including, but not limited to, asthma, cystic fibrosis, inflammation of the lungs secondary to ischemia of the gastrointestinal system, adult respiratory distress syndrome, and other allergic and inflammatory reactions of the pulmonary system including inflammation of the tissues of the upper respiratory system, allergic rhinitis, and respiratory distress syndrome; inflammation of the gastrointestinal system including, but not limited to, Crohn's disease, eosinophilic gastroenteritis, peritonitis, ulcerative colitis, ulcers of the small bowel and stomach, esophagitis, inflammation of the stomach, inflammatory bowel disease; ocular inflammation; preservation of whole blood; preservation of tissues, cells, and organs for transplantation; and protection of mitochondria.

Another object of the present invention is to provide a method of applying an effective amount of the compositions of the present invention through injection, topical, oral, or aerosol administration, for the treatment of inflammation resulting from the bites of insects, reptiles, amphibians, and other animals, especially venomous animals, such as venomous snakes.

Another object of the present invention is to provide a composition and method for inhibition of platelet function.

It is an object of the present invention to provide a composition for prevention and treatment for acute and chronic rejection of transplants, and for treatment of graft-vs-host disease and autoimmune diseases.

It is another object of the present invention to provide a composition for the treatment of neoplastic disease.

It is another object of the present invention to provide an easy to use topical therapeutic composition and topical treatment for various forms of arthritis and other inflammatory diseases, including, but not limited to, rheumatoid arthritis, inflammatory arthropathies, osteoarthritis, gout, and lupus.

It is another object of the present invention to provide a composition and treatment for parasitic infections including, but not limited to, toxoplasmosis, malaria, *Naegleria fowleri, Dilofilaria immitis*, nematodes, and pathogenic protozoans such as toxoplasma gondii, falciparum malaria, amebiasis, amoeba, and cryptosporidia.

It is another object of the present invention to provide the enhanced range of motion and reduced pain provided to patients with reflex sympathetic dystrophy following topical or oral application of the compositions of the present invention.

These and other objects, features and advantages of the present invention will become apparent after a review of the following detailed description.

DESCRIPTION OF THE PREFERRED EMBODIMENTS

The following applications are hereby incorporated by reference in their entirety: application Ser. No. 08/467,690 filed Jun. 6, 1995; application Ser. No. 08/475,335 filed Jun. 7, 1995; application Ser. No. 08/010,456 filed Jan. 27, 1993; application Ser. No. 07/839,780 filed Apr. 1, 1992; application Ser. No. PCT/US90/04615 filed Aug. 16, 1990; application Ser. No. 07/399,941 filed Aug. 29, 1989; application Ser. No. 07/256,330 filed Oct. 11, 1988; application Ser. No. 07/156,739 filed Feb. 18, 1988; and application Ser. No. PCT/US87/00408 filed Feb. 24, 1987.

Cis-unsaturated, but not saturated fatty acids, inhibit in vitro PLA$_2$ activities derived from human platelets and human polymorphonuclear leukocytes (PMNs). PLA$_2$ activity is inhibited by oleic, linoleic, and arachidonic acids to approximately the same extent indicating that the presence of a single cis-double bond is as inhibitory as multiple cis-double bonds. In contrast, fatty acids containing trans-double bonds or methyl esters of cis-unsaturated fatty acids are less inhibitory of PLA$_2$ activity. Thus, it is hypothesized that the preferred structural characteristics for inhibition of in vitro PLA$_2$ activity by unesterified fatty acids include at least one double bond. Oleic acid inhibits in vitro PLA$_2$ activity due to the presence of a single double bond at the C-9 position. Oxidation of the sarcoplasmic reticulum of muscle and of phospholipid membranes predisposes them to phospholipase degradation. Phospholipid membranes that have been oxidized at particular sites may appear intact and maintain functional activity, but their oxidation makes them vulnerable to degradation and destruction by $PLA_2$ or other phospholipases from endogenous or exogenous sources.

The observations illustrating the enhanced vulnerability of phospholipid membranes to phospholipase following oxidative and free radical mediated changes in cell membranes and/or cisunsaturated fatty acids have been employed in accordance with the present invention in the design of novel anti-inflammatory and cytoprotective agents. The present invention thus provides a biochemical and synthetic organic approach to controlling the expression of $PLA_2$ enzymes which is vital to the maintenance of membrane structure.

Although not wanting to be bound by the following hypothesis, it is believed that the number of available methylene interrupted unsaturated double bonds is directly related to the susceptibility of fatty acids to oxidation. This governs the ability of unsaturated fatty acids to act as anti-oxidants. This property, in conjunction with the anti-$PLA_2$ activity of the fatty moiety compounds of the present invention, markedly expands the scope of the anti-inflammatory and cytoprotective activity of the new agents disclosed herein. It is the property of the dual action of those compounds, i.e., their action as $PLA_2$ inhibitors with varying anti-oxidant activity, that provides the spectrum of anti-inflammatory activity in model systems that have direct applicability to cytoprotection and the control of inflammation and pathophysiology.

A nonfunctional alkyl chain or group is known as a hydrocarbon group because it contains only C-C and C-H single bonds. A nonfunctional alkyl chain therefore contains the maximum possible number of hydrogens per carbon which may be represented as $—C_nH_{2n+1}$. A functionalized alkyl chain or group has substituted for one or more hydrogens on the alkyl chain, one or more atoms or groups of atoms that have characteristic chemical behavior. These atoms or groups of atoms that have characteristic chemical behavior are also known as functional groups. Included in these functional groups are $C=C$, $OH$, $COOH$, $SO_3H$, $PO_3H$, $NH_2$, $—O—$, and halides.

In summary, a single double bond in a fatty moiety compound is sufficient to inhibit $PLA_2$ activity in vitro and in situ. The addition of multiple double bonds provides the additional value of an increase in potent anti-oxidant activity along with $PLA_2$ inhibitory action. The present invention thus provides compounds characterized by both anti-$PLA_2$ and varying anti-oxidant activity to maximize the anti-inflammatory and cytoprotective action which is the key to the clinical value of the compounds of the present invention.

In addition to inhibiting $PLA_2$ activity, the anti-oxidant action of these compounds protects proteins that become increasingly vunerable to attack by proteases due to oxidation. Thus, the cytoprotective $PLA_2$ inhibitors of the present invention, which have anti-oxidant activity as well, have value both in stabilizing membrane phospholipid and in inhibiting or preventing protein degradation or denaturation. This suggests that the compounds of the present invention act to minimize inflammation at its onset and will also interrupt the inflammatory process in progress.

The compounds of the present invention block arachidonic acid release from human polymorphonuclear cells and endothelial cells, a reaction mediated by cellular and secretory $PLA_2$ activity. Thus, the compounds of the present invention are potent, reversible $PLA_2$ inhibitors, and, as such, these agents inhibit the proinflammatory response of the human PMN and other inflammatory cells by inhibition of cellular and secretory $PLA_2$ activity. In addition, the compounds of the present invention inhibit, to various extents, the free radical activity in cells and tissues involved in the inflammatory process.

In a general sense, the present invention provides pharmacologically active, anti-phospholipase compounds. Preferably the compounds of the present invention are water or lipid soluble antioxidants. The preferred compounds have at least two fatty moieties and contain at least one unsaturated double bond. The fatty moieties may be different from each other in several features including, but not limited to, chemical composition, functional groups, the degree of unsaturation, and the length of the hydrocarbon chain. The compounds may also have at least one organic group, one active acid group or any salt form or ionized form thereof. The invention contemplates a variety of configurations including oligomers such as dimers, trimers, tetramers, and combinations thereof. Several of these compounds provided in accordance with principles and concepts of the present invention may be prepared as outlined in the following specific examples.

The compounds of the present invention are not generally hydrolyzed by pancreatic enzymes and are different from glycerol-based compounds in terms of their chemistry and metabolism. For example, we have observed that two compounds of the present invention, PX-13 and PX-18, are resistant to degradation in vitro by the commercially available pancreatic enzyme preparation, pancreatin, obtained from Sigma Chemical Company (St. Louis, Mo.). The resistance of PX-13 and PX-18 to metabolism by pancreatic enzymes supports their stability after oral administration.

The oligomers (dimers, trimers, tetramers, pentamers, etc.) of unsaturated fatty acids and the other compounds having at least one unsaturated straight chain fatty radical as described above, affect fundamental membrane phospholipid reactions of phospholipase-induced degradation and free radical peroxidation. The data set forth herein confirm with experimental results that these compounds are potent anti-inflammatory and cytoprotective agents.

The appropriate dosage of an effective amount of the unsaturated fatty moiety compounds of the present invention for treatment of mammals including humans, against phospholipase mediated injury and/or inflammation should be in the range of approximately 1 to 75 mg per kg (mg/kg) of body weight and preferably approximately 2 to 50 mg/kg of body weight, with a more preferable range of approximately 10 to 40 mg/kg of body weight, when the compound is administered orally or intraperitoneally (IP). When administered intravenously the dosage should be approximately 50% of the oral or IP dosage to achieve the same level of the drug in the blood. The described dosage is also be appropriate for prevention of human platelet aggregation or blood clotting. As is known to those skilled in the art, therapeutic doses expressed in terms of amounts per kilogram of body weight or surface area may be extrapolated from mammal to mammal, including to human beings. The compounds of the present invention may also be administered in an aerosol manner, such as an intranasal spray to treat inflammation of the nasal cavities, nasopharynx and adjacent regions or as inhaled formulations to treat inflammation of the upper and lower respiratory system.

The compositions of the present invention may be formulated for administration in any convenient way by analogy with other topical compositions adapted for use in mammals. These compositions may be used in any conventional manner with the aid of any of a wide variety of pharmaceutical carriers or vehicles. The compounds of the present invention described above can be provided as pharmaceutically acceptable formulations using formulation methods known to those of ordinary skill in the art. These formulations can be administered by standard routes. In general, the combinations may be administered by the topical, transdermal (including ionophoretic administration), buccal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441–446 (1991)

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include, but are not limited to, water, ethanol, acetone, glycerin, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | |
|---|---|
| Water/glycol mixture (15% or more glycol) | 50–99 parts by weight |
| Fatty Alcohol | 1–20 |
| Non-ionic Surfactant | 0–10 |
| Mineral Oil | 0–10 |
| Typical Pharmaceutical Adjuvants | 0–05 |
| Active Ingredients | 0.0001–10 |

A "classical" ointment is a semi-solid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | |
|---|---|
| White Petrolatum | 40–94 parts by weight |
| Mineral Oil | 5–20 |
| Glycol Solvent | 1–15 |
| Surfactant | 0–10 |
| Stabilizer | 0–10 |
| Active Ingredients | 0.0001–10 |

Additionally, the compounds may be formulated as oral, parenteral, subcutaneous, intravenous, intraarticular, intramuscular, intraperitoneal, intralesional and otherwise systemic compositions. Depending on the intended mode, the compositions may be in the form of solid, semi-solid, or liquid dosage forms, such as, for example, tablets, suppositories, pills, capsules, powders, liquids, suspensions, or the like, preferably in unit dosage forms suitable for single administration of precise dosages.

The compositions will include a conventional pharmaceutical carrier or excipient and a therapeutically effective amount of a compound of the present invention and, in addition, may include other medicinal agents, pharmaceutical agents, carriers, adjuvants, etc.

The amount of active compound administered will, of course, be dependent on the human or animal subject being treated, the severity of the affliction, the manner of administration and the judgment of the prescribing clinician.

Typical compositions contain approximately 0.01–95% by weight of active ingredient, with the balance one or more acceptable non-toxic carriers. The percentage of active ingredient, will, of course, depend upon the dosage form and the mode of administration.

For solid compositions, conventional non-toxic solid carriers including, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols and propylene glycol, as the carrier. Liquid pharmaceutically administerable compositions can, for example, be prepared by dissolving, dispersing, etc. an active compound as defined above and optional pharmaceutical adjuvants in a carrier, such as water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine, sodium acetate, triethanolamine oleate, etc. Actual methods of preparing such dosage forms are known, or will be apparent, to those skilled in this art, for example, see *Remington's Pharmaceutical Sciences,* Mack Publishing Company, Easton, Pa., 15th edition, 1975. The composition or formulation to be administered will, in any event, contain a quantity of the active compound(s) in an amount effective to alleviate the symptoms of the subject being treated.

For oral administration of the compounds of the present invention, a pharmaceutically acceptable non-toxic composition is formed by the incorporation of any of the normally employed excipients, such as pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 2%–95% active ingredient, preferably 5%–90%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

Ointments for topical application may be prepared by incorporating approximately 0.1 to 10% of the compound as an oil or salt form into an ointment base containing emulsifying agents such as stearic acid, triethanolamine and/or cetyl alcohol. The formulation may also include ingredients such as glycerol, petrolatum, water and preservatives as required.

Water based lotions may contain the compounds of the present invention as an oil or solid in amounts ranging from approximately 0.1% to 5.0% by volume. Such lotions may contain glycerine and/or bentonite as suspending agents as is well known in the art. The present invention may also be incorporated into creams.

The compounds may also be incorporated into classical (one or two phase) or non-classical (aqueous emulsion) aerosol formulations. Such formulations include the compounds and an appropriate propellant carrier in which the compounds are dissolved or dispensed. In the classical form the active ingredients are generally used as an oil dispersion or in solution in an organic solvent such as ethanol. In the non-classical form the active ingredient is dissolved in water. In each case the concentration of the active ingredient in the carrier may be about approximately 0.1 to 10% by weight or volume.

Of particular advantage is the fact that the unsaturated straight chain fatty moiety compounds described above function pharmacologically at the site of inhibitory action for the arachidonate cascade and preferentially affect stimulus-induced mobilization of arachidonate. Inhibition of $PLA_2$ depresses the production of both prostaglandins and leukotrienes in stimulated or inflamed cells. Importantly, the compounds described above have a much more pronounced effect on stimulus-induced, than on controlled release of arachidonate indicating a selective effect on the former. Moreover, when phospholipids are peroxidized, the polymer compounds described above are capable of inhibiting the degradation of such lipids by lysosomal phospholipase C, indicating that these compounds can protect already damaged (oxidized) membranes.

Thus multiple actions are responsible for the anti-inflammatory activity of the fatty moiety compounds of the present invention, and on the basis of inflammatory models, it is evident that these compounds can effectively rival or replace both currently available steroids and NSAIDs in the treatment of inflammation, making the fatty moiety compounds of the present invention candidates for clinical application and usefulness in localized and systemic injury and disease.

The fatty moiety compounds described above, by protecting lipid membranes and possessing anti-oxidant activity, are potent anti-oxidants for preservation, not only of living cells and tissues, but their action makes them effective as preservatives of biological materials from animal, human or plant origin, and as preservatives of chemical agents subject to oxidative injury. For purposes of protecting and preserving biological materials subject to oxidation injury, the fatty moiety compounds of the present invention may be used at concentrations of approximately 0.1 to 100 $\mu$M. These molarities are calculated as the molarity that would be obtained if the drug were dissolved in a weight of water which is the same as the weight of the biological material to be preserved. For example, in vitro, anti-oxidant and/or anti-phospholipase applications, concentrations of from about approximately 0.1 to about 500 $\mu$M should be effective.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Ricinoleic Acid Related Compounds

In one preferred form, the compound may be a derivative of ricinoleic acid having a structural configuration as set forth below

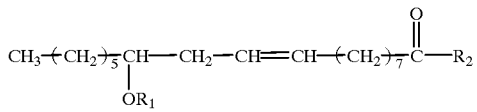

where $R_1$ is an alkyl group or acyl group, which may be functionalized or non-functionalized, which includes an active acid group or salt form thereof, and $R_2$ is an alkoxy or alkylamino group which includes one of the fatty moieties. More particularly, in the foregoing compound, $R_2$ may be

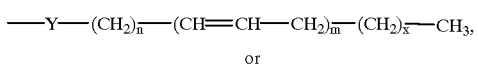

or

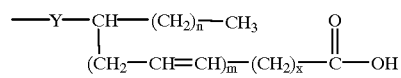

wherein n is an integer from 1 to 18, m is an integer from 1 to 4, x is an integer from 0 to 12, and Y is —O— or —NH—, or —NR— wherein R is a functionalized or non-functionalized alkyl group of 1 to 6 carbons.

In one case the $R_1$ moiety may be obtained by esterification of the 12-position hydroxy group of ricinoleic acid with an acid group of a divalent acid such as sebacic acid, fumaric acid, maleic acid, oxalic acid, succinic acid, or organic moieties including, but not limited to, ethylenediamine tetraacetic acid (EDTA) and its analogs and derivatives, and the $R_2$ moiety may be obtained by esterification of the 1-position carboxy group of ricinoleic acid with the hydroxyl group of another ricinoleic acid molecule or of some other fatty alcohol such as, for example, oleyl alcohol, linoleyl alcohol, linolenyl alcohol, arachidonyl alcohol or cis-5, 8, 11, 14, 17-eicosapentaenyl alcohol. Alternatively, the $R_2$ moiety may be obtained by amidification of the 1-position carboxy group of ricinoleic acid with the amine group of an unsaturated fatty amine such as oleyl amine, linoleyl amine, linolenyl amine, arachidonyl amine or cis-5, 8, 11, 14, 17-eicosapentaenyl amine.

EXAMPLE 2

Alternatively, the compounds of the present invention may have the generic structural formula as set forth below;

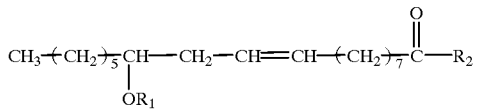

however, in this case $R_1$ may be an alkyl group which may be functionalized or non-functionalized and includes an active acid group or one of the fatty moieties, and $R_2$ may be either a hydroxy group or an alkoxy group which includes fatty moieties. In this alternative case, when $R_2$ is a hydroxy group, $R_1$ may be derived by esterification of the 12-position hydroxy group of the ricinoleic acid, with, for example, the acid group of oleic acid, linoleic acid, linolenic acid, arachidonic acid or cis-5, 8, 11, 14, 17-eicosapentaenoic acid. Thus, in this case, $R_1$ may be a fatty moiety having one of the following configurations:

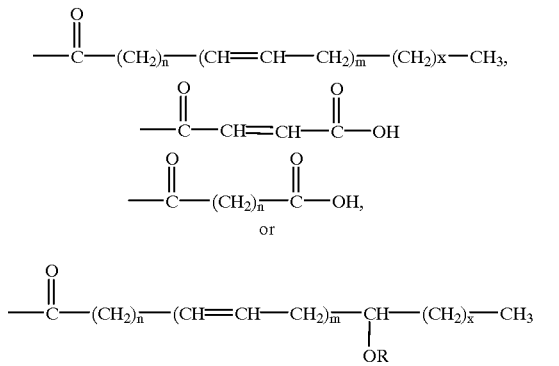

where n is an integer from 1 to 18, m is an integer from 1 to 4, x is an integer from 0 to 12, and R is H a fatty moiety or an alkyl group which may be functionalized or non-functionalized.

The invention contemplates compounds of a variety of configurations including, for example oligomers including dimers, trimers, tetramers and combinations thereof. Dimers of ricinoleic acid are prepared for example, by esterifying the 12-position hydroxy groups of two molecules of ricinoleic acid with the carboxy groups of a diacid such as sebacic acid, fumaric acid, maleic acid, oxalic acid or succinic acid.

A trimer of ricinoleic acid is prepared, for example, by esterifying the 12-position hydroxy groups of three molecules of ricinoleic acid with the carboxy groups of a tri-acid such as cis-aconitic acid.

A tetramer of ricinoleic acid is prepared, for example, by esterifying the 12-position hydroxy groups of four molecules of ricinoleic acid with the carboxy groups of a tetra-acid such as ethylenediaminetetraacetic acid.

Various compounds may be linked together by esterification through one of the free acid groups. Thus, the acid groups may be converted to acid chloride groups and reacted with hydroxy or amine groups of a divalent compound.

In each case, the compounds of the present invention include at least one unsaturated bond and at least two fatty moieties. Desirably, each compound may also include at least one active acid group or any ionized form or salt form thereof. Some of the preferred acid groups include but are not limited to sulfonyl, sulfonate, phosphoryl, phosphonate, carboxyl and carboxylate.

EXAMPLE 3

Synthesis of N,N-Bis(oleic acid-12-oxycarbonylmethyl)-N-N'bis(carboxylmethyl) ethylenediamine This compound is represented by the following structural configuration:

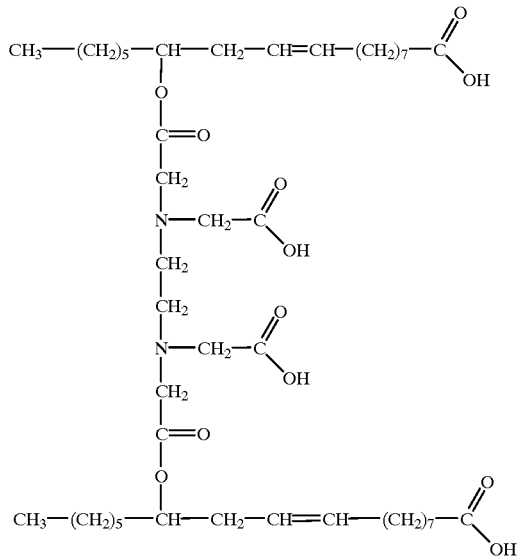

To 6.22 g (20.8 mmol) of ricinoleic acid and 4.00 g of triethylamine in 150 mL THF was added 2.31 g (9.0 mmol) of ethylenediamine tetraacetic acid dianhydride. After stirring 15 min at 40° C., 20 mL of acetonitrile was added, since ethylenediamine tetraacetic acid dianhydride was not dissolved completely. The solution was stirred for 72 h under reflux and gradually turned yellow during this time. The solvent was removed under reduced pressure. The mixture was suspended in 100 mL of ether and extracted twice with 50 mL of saturated aqueous sodium chloride. After drying the ether solution, the solvent was removed under reduced pressure. The residue was suspended in methanol and filtered. The solvent was removed under reduced pressure. The residual oil was purified by chromatography on silica gel, eluted with a gradient of acetone/methanol (70:30 v/v to 0:100 v/v). N,N-bis(oleic acid-12-oxycarbonylmethyl)-N-N'-bis(carboxylmethyl) ethylenediamine was isolated as a yellow solid with a yield of 1.23 g (14%). This compound is readily soluble in water.

N,N-Bis(oleic acid-12-oxycarbonylmethyl)-N-N'bis (carboxylmethyl) ethylenediamine exhibits an $EC_{50}$ value of 5 to 10 μM in the inhibition of $PLA_2$ activity.

EXAMPLE 4

1,3-Bis(12-hydroxyoleoylamino)-2-hydroxypropane

This compound is represented by the following structural configuration:

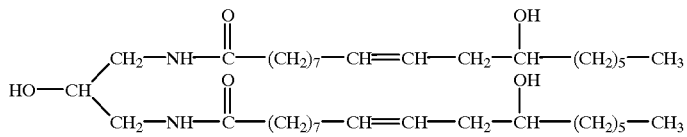

To a solution of 12.60 g (31.9 mmol) of ricinoleic acid N-hydroxysuccinimide ester and 1.8 g (20 mmol) of 1,3-diamino2-hydroxypropane in 125 mL of methylene chloride was added a catalytic amount of sodium bicarbonate. The suspension was stirred for 48 h at 35° C. The mixture was filtered and the solvent was removed under reduced pressure. The oil was suspended in water and extracted 3 times with methylene chloride. The solvent was removed and the yellow heavy viscous oil was dried in vacuo. The yield was 930 mg.

EXAMPLE 5
1,3-Bis(oleoylamino)-2-hydroxypropane

This compound is represented by the following structural configuration:

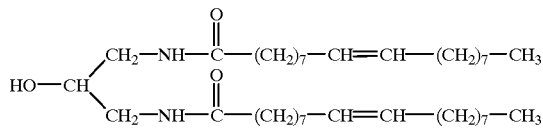

To a solution of 8.60 g (95.4 mmol) of 1,3-diamino-2-hydroxypropane in 400 mL of water was added 200 mL of methylene chloride. The emulsion was cooled to 0° C. and 85.0 g (280 mmol) of 85% oleoyl chloride were added. The mixture was stirred vigorously for 1 h at 0° C. and for 1 h at room temperature. The resulting precipitate was recovered by filtration and was dried in vacuo. Reprecipitation from ethanol provided a white solid with a yield of 31.10 g (53%) and a melting point of 91–92° C.

EXAMPLE 6
1,3-Bis(oleoylamino)-2-propyl succinic acid monoester

This compound is represented by the following structural configuration:

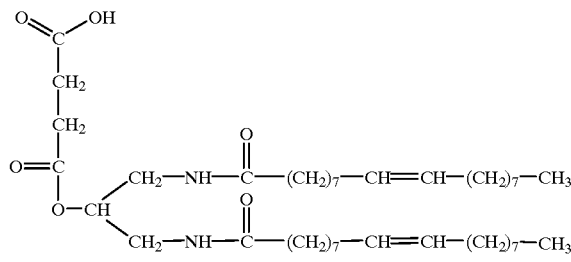

To a solution of 505 mg (0.817 mmol) of 1,3-bis (oleoylamino)-2-hydroxypropane and 140 mg (1.40 mmol) of succinic anhydride in 20 mL of acetonitrile and 20 mL of THF was added 5 mL of triethylamine. The suspension was stirred at 35° C. After 15 min succinic anhydride was completely dissolved. The solvent was removed under reduced pressure after 48 h. The yellow oil was suspended in water and extracted three times with ether. The solvent was removed under reduced pressure and the yellow oil 1,3 bis(oleoylamino)-2-propyl succinic acid monoester was dried in vacuo. The yield was 380 mg (65%).

In addition to the foregoing compounds, some of which comprise derivatives of ricinoleic acids, additional compounds are included within the broad scope of the present invention. Some of these compounds are defined structurally by the following Examples.

EXAMPLE 7

One such class of compounds is defined by the following generic formula,

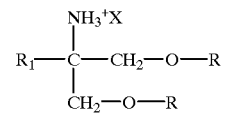

wherein X is an organic or inorganic anionic moiety such as bicarbonate, acetate, citrate, succinate, p-toluenesulfonate (Example 13), or halide such as chloride, fluoride, bromide or iodide, or phosphate, sulfate and other pharmaceutically acceptable anions; wherein $R_1$ is —$CH_2$—O—R, a hydrogen, or an alkyl group or chain which may be functionalized; and wherein the R groups may be the same or different and each R group is a fatty moiety. In this form of the present invention the R groups may have the following structural formulation:

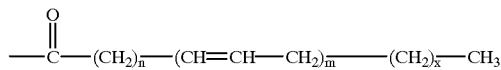

where n is an integer from 1 to 18, m is an integer from 1 to 4, x is an integer from 0 to 12, and the R groups may be the same or different.

A method for preparing a particularly preferred compound having the foregoing structural configuration, p-toluene sulfonic acid salt of tristrioleate, is described in Example 13.

EXAMPLE 8
Generic TES Related Compounds

Alternatively, the compounds of the present invention may have the generic formula:

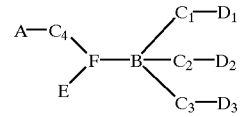

In this structure, A comprises H, OH, a sugar moiety, an ether, an ester, an amide or $NH_2$, or an acid or salt thereof. Some of the preferred acids that may be substituted for A include but are not limited to COOH, $SO_3H$ or $PO_3H$.

B is a connecting group selected from the group consisting of C, —$(CH_2)_nC$—, $N^+$, and $(CH_2)_n$ $N^+$ wherein n is an integer from 1 to 24, and the —$(CH_2)_n$ chain may be functionalized or non-functionalized.

$C_1$, $C_2$, $C_3$ and $C_4$ are connecting groups selected from the group —$(CH_2)_n$— where n is an integer from 1 to 24, wherein the —$(CH_2)_n$— chain may be functionalized or nonfunctionalized. $C_1$, $C_2$, $C_3$ and $C_4$ may also be selected from the group consisting of poly(ethylene oxide) of the formula $(CH_2-CH_2-O)y$ wherein y is an integer from 1 to 12. $C_1$, $C_2$, $C_3$ and $C_4$ may be the same or different.

$D_1$, $D_2$ and $D_3$ are fatty chains consisting of fatty acid esters of the form $CH_3(CH_2)_n COO$ or fatty acid amides of the form $CH_3(CH_2)_n CONH$ wherein n is an integer from 0 to 32. At least one of the fatty chains is unsaturated at one or more positions, and $D_1$, $D_2$ and $D_3$ may be the same or different with respect to length and degree of unsaturation. $D_1$, $D_2$ or $D_3$ may also be H provided no more than one of $D_1$, $D_2$ and $D_3$ is H in any one compound. In the generic formula listed above, the fatty acid chains of the molecule may be comprised of $(CH_2)_n$ wherein n is an integer from 1 to 32. These fatty acid chains may each be unsaturated at one or more sites and may be of different lengths from 1 to 32 carbon atoms.

E is H, or is the same as A-$C_4$, or is $CO(CH_2)_n CH_3$ or $CO(CH_2)_n COOH$ where n is an integer from 0 to 24. The alkyl $(CH_2)_n$ chain may be functionalized or nonfunctionalized.

F is selected from the group consisting of N, NR, P, P=O, CH or CR, wherein R is an alkyl chain of 1 to 6 carbons which may be functionalized or non-functionalized.

More specifically, the compounds may also have the formula.

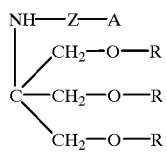

wherein the R groups may be the same or different and each R is a fatty moiety as set forth below,

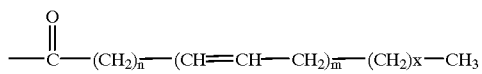

wherein n is an integer from 1 to 18, m is an integer from 1 to 4, and x is an integer from 0 to 12.

In this form of the present invention Z represents a $C_1$ to $C_5$ aliphatic moiety, which may be functionalized or non-functionalized, and A represents an organic acid moiety or salt form thereof or any organic acid radical. It is to be understood that the acidic groups and the NH groups in the generic structure described above may be present in ionized form. Some of the preferred acid groups that may be substituted for A include but are not limited to COOH, $SO_3H$ or $PO_3H$.

EXAMPLE 9

Synthesis of 2-[Tris(oleoyloxymethyl)methylamino]-1-ethanesulfonic acid also called PX-13 or TES Trioleate To a 250 ml single-neck, round-bottom flask 1.0 g (4.26 mmoles) of 2-[tris(hydroxylmethyl)methylamino]-1-ethanesulfonic acid (TES; Aldrich; 99% purity) and 25.0 mL of anhydrous dimethyl formamide (DMF) were added. The flask contents were then cooled to 0° C. in an ice-water bath. Oleoyl chloride (Aldrich, technical grade) 5.25 g (17.45 mmoles), was added dropwise over a 5 minute period. The reaction mixture was stirred at room temperature for 4 days. We have also performed this reaction by stirring for a shorter period of time at elevated temperatures. The DMF was removed at 40–45° C. under reduced pressure. The residue was a viscous oil which was transferred to a flask containing 200 mL acetone and vigorously stirred until a slightly cloudy solution formed. This solution was refrigerated overnight. The precipitate formed was collected by filtration and thoroughly extracted with distilled acetone (20 mL) five times. The product was dried in vacuo at room temperature for 24 h producing a yield of 2.32 g (52%), and has the following structural configuration:

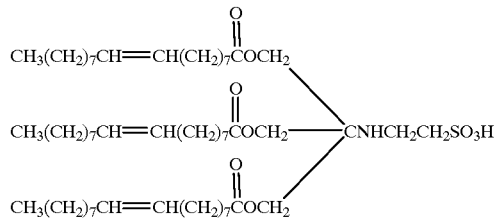

Another method of synthesizing 2-[Tris (oleoyloxymethyl) methylamino]-1-ethanesulfonic acid is provided in the following paragraph.

To 49.0 g (219 mmol) of 2-[tris(oleoyloxymethyl) methylamino]-1-ethanesulfonic acid in 500 mL of $CH_3CN$ was added 385 mL (990 mmol) of 85% oleoyl chloride. The orange-brown suspension was stirred under nitrogen at 35° C. for 36 h. Then 500 mL of acetone were added into the brown suspension. The reaction mixture was put in the freezer overnight. The light brown solid was reprecipitated from ethanol, then from methanol/acetone (approximately 1:9) and from ethanol again. The white solid was dried in vacuo. The yield was 152.2 g (70%) and the melting point was 62–64° C.

EXAMPLE 10

Synthesis of N-[Tris(oleoyloxymethyl)methyl]-N-(2-sulfoethyl) succinic acid monoamide This compound is represented by the following structural configuration:

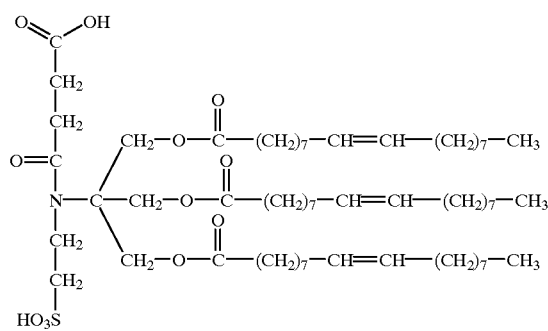

To 566 mg (0.553 mmol) of 2-[tris(oleoyloxymethyl) methylamino]-1-ethanesulfonic acid in 10 mL THF was added 410 mg (4.06 mmol) of triethylamine. After 5 min 96 mg (0.960 mmol) of succinic anhydride was added. The yellow solution was stirred for 18 h under reflux. The solvent was removed under reduced pressure. The residual oil was purified by chromatography on silica gel, eluted with an ethyl acetate/methanol gradient (25:75 vol/vol to 0:100 vol/vol). N-[tris(oleoyloxymethyl)methyl]-N-(2-sulfoethyl) succinic acid monoamide was isolated as a yellow heavy viscous oil with a yield of 240 mg (38%).

EXAMPLE 11

Synthesis of N-[Tris(oleoyloxymethyl)methyl]-N-(2-sulfoethyl) tartaric acid monoamide

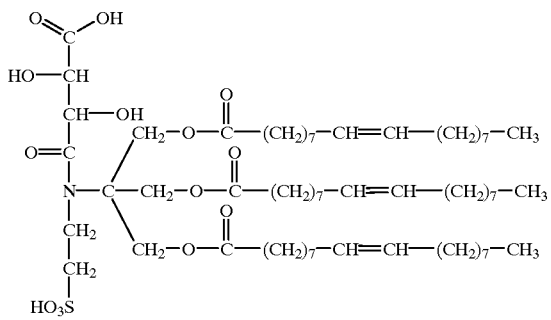

Synthesis of N-[tris(oleoyloxymethyl)methyl]-N-(2-sulfoethyl) tartaric acid monoamide was accomplished in two steps. First, reaction of 2-[tris(oleoyloxymethyl) methylamino]-1-ethanesulfonic acid with diacetyltartaric acid anhydride resulted in N-[tris(oleoyloxymethyl)methyl]-N-(2-sulfoethyl)-2,3-diacetyltartaric acid monoamide. This was hydrolyzed with sodium hydroxide to yield N-[tris (oleoyloxymethyl)methyl]-N-(2-sulfoethyl) tartaric acid monoamide. The reaction is described in detail below.

First the synthesis of N-[tris(oleoyloxymethyl)methyl]-N-(2-sulfoethyl)-2,3-diacetyltartaric acid mono amide was performed by adding added 1.23 g (11.6 mmol) of triethylamine to 2.07 g (2.02 mmol) of 2-[tris(oleoyloxymethyl) methylamino]-1-ethanesulfonic acid in 150 mL THF. After 5 min 793 mg (3.66 mmol) of diacetyltartaric anhydride was added. The yellow solution was stirred for 18 h under reflux. The solvent was removed under reduced pressure. The residual oil was purified by chromatography on silica gel, eluted with an ethyl acetate/methanol gradient (20:80 vol/vol to 0:100 vol/vol) and a trace of acetic acid. N-[tris (oleoyloxymethyl)methyl]-N-(2-sulfoethyl)-2,3-diacetyltartaric acid monoamide was isolated as a yellow heavy viscous oil with a yield 1.36 g (56%).

Next, to 1.30 g (1.05 mmol) of N-[tris(oleoyloxymethyl) methyl]-N-(2-sulfoethyl)-2,3-diacetyltartaric acid monoamide in 50 mL THF was added 20 mL 0.5 aqueous sodium bicarbonate. After 60 min treatment with ultrasound the solvent was removed under reduced pressure. The residual mixture was suspended in water and extracted with ether. N-[Tris(oleoyloxymethyl)methyl]-N-(2-sulfoethyl) tartaric acid monoamide was isolated as a yellow heavy viscous oil with a yield of 1.12 g (92%).

EXAMPLE 12

Tris(oleoyloxymethyl)methylamine p-Toluene Sulfonic Acid

Tris(hydroxymethyl) aminomethane (Tris, Aldrich) 0.54 g (4.4 mmoles), 5.0 g (17.7 mmoles) of oleic acid (Aldrich), and 1.26 g (6.6 mmoles) of p-toluenesulfonic acid monohydrate (Sigma) were mixed in 50 mL of toluene and placed in a 100 mL round-bottomed single-necked flask equipped with a Dean-Stark trap and a Teflon-coated magnetic stirring bar. After bubbling the reaction mixture with $N_2$ gas for 10 minutes, the reaction mixture was stirred and heated to reflux. The reaction was continued until a stoichiometric amount of water was recovered (0.38 ml). After removal of a small amount of undissolved material by filtration, the toluene was removed by rotoevaporation to yield a white waxy product. This product was purified on a silica gel column (Aldrich 230–400 mesh, 2.0×55 cm) with 8:2 petroleum ether (bp 60–90° C.)—ethyl acetate as developing solvent. After eluting with developing solvent the top uncolored layer was carefully removed and the product extracted with ethyl acetate from the silica gel. The solvent was removed by rotoevaporation and the product recovered as a tris(oleoyloxymethyl)methylamine p-toluene sulfonic acid having the following structural configuration:

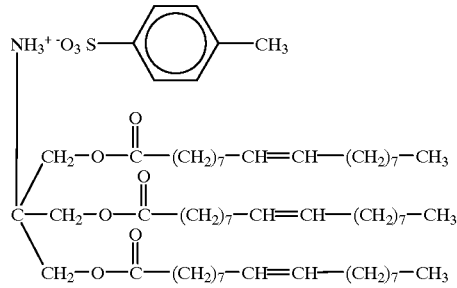

In this procedure, the amine group of the Tris is protected from reacting with the fatty acid because it is in the form of a p-toluene sulfonate salt. Moreover, the p-toluene sulfonic acid acts as a catalyst for the esterification between the alcohol functions on the Tris and the fatty acid.

EXAMPLE 13

Generic Formula for PX-18 Related Compounds

These compounds are represented by the following structural configuration:

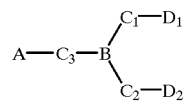

A comprises H, OH, a sugar moiety, an ether, an ester, an amide or $NH_2$, or an acid group or salt thereof. Some of the preferred acids include COOH, $SO_3H$, and $PO_3H$.

B is N, NR, P, P=O, CH or CR wherein R is an alkyl chain of 1 to 6 carbons which may be functionalized or non-functionalized.

$C_1$, $C_2$ and $C_3$ are connecting groups selected from the group consisting of —$(CH_2)_n$— wherein n is an integer from 1 to 24, and the —$(CH_2)_n$— chain may be functionalized or non-functionalized. $C_1$, $C_2$ and $C_3$ may also be selected from the group consisting of poly(ethylene oxide) of the formula $(CH_2CH_2$—O$)y$ wherein y is an integer from 1 to 12. $C_1$, $C_2$ and $C_3$ may be the same or different.

$D_1$ and $D_2$ are fatty acid chains consisting of fatty acid esters of the form $CH_3(CH_2)_n$ COO or fatty acid amides of the form $CH_3(CH_2)_n$ CONH wherein n is an integer from 1 to 32. At least one of the fatty chains is unsaturated at one or more positions, and $D_1$ and $D_2$ may be the same or different with respect to length and degree of unsaturation.

In the generic formula listed above, the fatty acid chains of the molecule may be comprised of $(CH_2)n$ wherein n is an integer from 1 to 32. These fatty acid chains may each be unsaturated at one or more sites and may be of different lengths from 1 to 32 carbon atoms.

EXAMPLE 14

BES Dioleate, also called PX-18 or 2-[N,N-Bis(2-oleoyloxyethyl)amino]-1-ethanesulfonic acid A preferred embodiment of the generic structure in the preceding Example is represented by the following structural configuration:

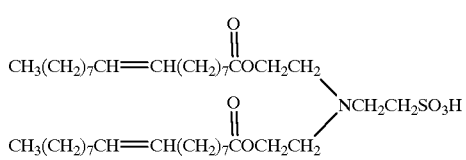

In the formula for PX-18 shown above, the $SO_3H$ acid group may also be in the salt form or in an ionized form.

N,N-Bis(2-hydroxyethyl)-2-aminoethane sulfonic acid was prepared (according to Izumi, 1954) by refluxing an aqueous solution of sodium 2-bromoethanesulfonate with 2 equivalents of diethanolamine for 2 hours. The cooled reaction mixture was passed over a sulfonic acid resin (Dowex 50) in the acid form. The eluate, containing product and HBr, was taken to dryness at reduced pressure and the product was recrystallized from aqueous alcohol. The yield was 52% and the compound had a melting point of 153–155° C.

In a 1 liter round bottomed flask, 16.2 g (0.076 mol) of N,N-bis(2-hydroxyethyl)-2-aminoethane sulfonic acid were dissolved in a solution of 60 mL of DMF and 36 mL of triethyl amine. To this solution 72 g (0.239 mol) of oleoyl chloride (85% Aldrich) were slowly added under a $N_2$ atmosphere with stirring. (During the addition of the oleoyl chloride a precipitate is produced). After all of the oleoyl chloride was added, 300 mL of acetone or THF was added to the mixture. The reaction mixture was allowed to stir under a $N_2$ atmosphere for 12 h. The precipitate was collected by a filtration, and then recrystallized from $CHCl_3$/$CH_3$ CN. A yellowish product (43.6 g) was obtained in 77% yield. The product was decolorized with charcoal in $CH_3Cl$, recrystallized from $CHCl_3$/$CH_3CN$, and exhibited a melting point of 133–136° C.

EXAMPLE 15
Topical Cream Formula and Formulation Including TES Trioleate (4% PX-13)

Ingredients for solution A are 8 g cetyl alcohol; 2 g oleic acid; 2 g isopropyl myristate 0.5 g paraben; 4 g PX-13. Ingredients for solution B are 78 ml $dH_2O$ (78 g); 1 g TRIS.HCl; 3.0 g SDS (sodium lauryl sulfate); 3 g sorbitol; 5 g 1,2 propanediol.

Formulation of Skin Cream

Formulation of solution A: In a 100 mL beaker cetyl alcohol was heated to melting (approximately 70° C.) and the oleic acid and isopropylmyristate are added and mixed together with the paraben. When these ingredients are in solution, the PX-13 was added and the temperature maintained at 70° C. until solution occurred.

Formulation of solution B: In 200 mL beaker the water was brought to boiling and then removed from the hot plate. TRIS.HCl and SDS were added and stirred until dissolved. The sorbitol and propanediol were then added with stirring in succession while maintaining the temperature at approximately 70° Next, solution B was rapidly stirred while solution A was slowly added. The mixture was thoroughly stirred (for about 5 min). While the mixture was hot (70° C.) 25 g was poured into 4 (1 oz) dispensing tubes.

It is understood that the formulation may optionally contain additives such as lanolin, aloe, herbal extracts, or various scents such as floral scents. Additionally, the formulation may optionally contain preservatives, antimicrobials, penetration enhancers and other skin cream ingredients commonly known to one skilled in the art.

EXAMPLE 16
Dermatologic Disorders

Studies were conducted with skin creams produced under GMP conditions containing PX-11 (tricinyl trioleate) and PX-13 and prepared according to the following recipe using ingredients known to one of ordinary skill in the art.

TABLE

|  | Base Cream | Experimental |
|---|---|---|
| d $H_2O$ | 92.5% | 87.5% |
| carbopol | 0.3 | 0.3 |
| glycerin | 2.0 | 2.0 |
| pollex | 2.0 | 2.0 |
| Finsolv | 2.0 | 2.0 |
| PX-11/13 (active) | — | 5.0 |
| Germaben 2E | 1.0 | 1.0 |
| AMP (amine) | 0.2 | 0.2 |

These products were used with four psoriatic and three atopic dermatitis volunteers. PX preparations applied topically to psoriatic lesions twice a day over a three-week period reduced swelling, diameter and elevation of plaques in all patients. In the atopic dermatitis patients there was also improvement including reduced erythema, itching and burning.

Evaluation of PX Compounds in Cream Formulations

Two PX compounds PX-11 and PX-13 were evaluated in a cream formulation prepared under GMP. The chemicals were formulated into a bland cream and evaluated in the following human or mouse skin tests: (1) occluded patch test for irritation; (2) cell turnover rate; (3) transepidermal water loss; (4) skin moisturization; and (5) reduction in erythema after induced sunburn.

The human skin tests were conducted on three volunteer female subjects, ages 29–32; a cream base with no added active was included as a control, while the untreated skin served as an additional basis for evaluation. Sunburn tests were performed on a total of 30 hairless albino mice. Results of the studies are summarized below.

1. Occluded patch test. Samples were applied on the subjects' backs between the scapulae and waist adjacent to the spinal column. Each site was sensitized to the chemicals by removal of half the stratum corneum barrier by tape stripping. The levels of irritation on the sensitized sites were measured after 24 hours of occluded exposure to the creams. The levels of erythema, edema, vesiculation and blister formation were scored. All samples were non-irritating.

2. Cell turnover rate: This parameter was measured by adsorption of dansyl chloride, in which 3% dansyl chloride was incorporated into petrolatum. This salve was applied over a 2.5 cm diameter circular area in the upper arm and a patch applied. 24 hours later the patch was removed. The intensity of dansyl chloride fluorescence was indicative of the cell turnover rate in the epidermis.

It was found that the control cream decreased cell regeneration time by 35%, i.e., the cells renewed more rapidly compared with the untreated skin (a skin patch with nothing applied). The addition of PX samples inhibited the rate of cell regeneration. In fact, for PX-11, the time to regenerate was longer than that observed for the untreated skin (see table below).

|  | Days to Cell Renewal | | % Change in Cell |
|---|---|---|---|
|  | Untreated | Treated | Turnover Time |
| PX-11 | 21.5 | 28.8 | +34 |
| PX-13 | 30.4 | 21.6 | −29 |
| Control | 30.4 | 19.7 | −35 |

Note that the control cream accelerates cell growth but in the presence of PX-11 and PX-13 cell growth is inhibited. For PX-11, growth is so severely retarded that the treated skin area requires significantly longer times for the cells to regenerate. These results suggest that PX compounds may be useful in the treatment of psoriasis.

3. Transepidermal water loss. This parameter was measured by affixing a flow cell on the forearm site, applying the cream, waiting 20 minutes, then flushing the volume with nitrogen and noting the moisture content of the effluent gases. It was found that PX-13 functioned as an occluding moisturizer, reducing the rate at which water is lost from the epidermal layer. The control and PX-11 opened the pores and permitted water to escape from the epidermal layer. PX-11 was 10 times more effective than the control at promoting water loss.

| % Change in Transepidermal Water Loss | |
| --- | --- |
| PX-11 | +649.0 |
| PX-13 | −8.5 |
| Control | +56.5 |

4. Skin moisturization. Skin moisturization was measured using 20 megahertz ultrasound (the presence of moisture produces a density decrease in the outer skin layers), before and 30 minutes after product application to the forearm. It was found that PX-11 exhibited good moisturization properties, while PX-13 and the control were not good moisturizers.

| Moisturization Effects | | | |
| --- | --- | --- | --- |
| | Ultrasound Density Score | | |
| Subject | PX-11 | PX-13 | Control |
| 1 | 3 | 1 | 2 |
| 2 | 3 | 2 | 1 |
| 3 | 1 | −1 | −2 |
| Total | 7 | 2 | 1 |

7 = Best; 1 = Baseline

5. Protection against ultraviolet-induced erythema. The protection against ultraviolet-induced erythema (i.e., the burn and irritation produced after exposure to ultraviolet radiation), was measured by first irradiating 12 mice with destructive 3130 angstrom (Å) rays, applying the creams, and then evaluating the skin cells for erythema. PX-11 was significantly better than the base cream in erythema reduction.

| Post-Radiation Erythema Rankings | | | |
| --- | --- | --- | --- |
| Subject | PX-11 | PX-13 | Control |
| 1 | 2 | 5 | 3 |
| 2 | 2 | 5 | 4 |
| 3 | 2 | 4 | 5 |
| Mean | 2 | 4.7 | 4 |

1 = Best; 4 = Worst

The results presented in Example 16 suggest that the PX test compounds were active in modifying human skin cell activity and, therefore, may impart beneficial effects when used as a skin cream in a variety of dermatologic and cosmetic conditions.

EXAMPLE 17

Neurological Inflammatory Conditions

While not wanting to be bound by this statement, it is believed that $PLA_2$-mediates inflammation and nerve tissue damage in spinal cord injury and sciatic-nerve inflammation and in a variety of central and peripheral neurological inflammatory conditions. The following experiments demonstrate antiinflammatory activity of PX compounds.

1. Activity of PX-13 to Inhibit $PLA_2$-Induced Inflammation in Mouse Paw Edema Tests Edema was induced by injection of 1 ug of purified human disc $PLA_2$ into the mouse footpad. PX-13 was administered either by gavage or intraperitoneally (IP) 60 min prior to enzyme challenge. Forty-five min after enzyme injection, the animals were sacrificed and the control and injected paws were removed and weighed to assess edema. The results are presented in the following table.

| PX-13 (mg/kg) | Percent Protection |
| --- | --- |
| 20 (gavage) | 33% |
| 40 (gavage) | 55% |
| 60 (gavage) | 63% |
| 40 (IP) | 48% |

PX-13 displays anti-inflammatory activity in this model when administered by gavage or IP.

2. Protective effects of PX-13 in Cultured Rat Dorsal Root Ganglion Cells Exposed to Snake Venom and Human Disc $PLA_2$ Primary cultures of rat dorsal root ganglion cells were used. Cells were washed 3-times with media to remove serum. Then, PX-13 (20 uM) in HEPES buffer or a buffer control was applied to the cells. After 10 min of incubation, purified human disc $PLA_2$ (activity 1 umol/min) was added and the cells were incubated for an additional 60–90 min. Cells were then observed, fixed, and photographed 1.5 hrs after addition of $PLA_2$.

Cells treated with PX-13 (20 uM) alone or PX-13+$PLA_2$ treated cells were indistinguishable from control cultures, whereas, extensive morphologic damage was induced by $PLA_2$ alone within 60 min; considerable cell blebbing and loss of texture was noted. PX-13 is cytoprotective in this system to a toxic dose of human disc $PLA_2$. PX-13 also protected against the toxicity induced by purified snake venom $PLA_2$ used in comparable amounts (1–3 umols/min/mg for 60 min).

These and other results support the concept that the high levels of secretory $PLA_2$ in herniated disc conditions can irritate nerves and may contribute to the generation of low back pain. These results suggest the potential efficacy of PX compounds in treating these and related neurological conditions.

3. Inhibitory Effect of PX-13 on Nucleus Pulposus (NP)-Induced Mouse Paw Edema

Human NP-homogenate was prepared according to the following protocol and stored frozen until use. Human vertebral discs were thawed and the tissue pieces were washed twice with isotonic saline. Tissue samples were homogenized in a minimum volume of isotonic saline using a Brinkman homogenizer. This homogenate was filtered through two layers of cheesecloth and the resultant filtrate was subjected to Dounce homogenization. This homogenate was again filtered through two layers of cheesecloth and the filtrate was capable of passing through a 26-gauge needle; 50 ul of the filtrate was administered to each mouse paw.

The filtrate contained 1.57 mg/ml of protein and its $PLA_2$ activity was 12.8% hydrolysis of 10 nmols of *E.coli* phospholipid/10 ul filtrate/30 min. incubation at 37° C. Therefore, each mouse paw received 78.5 ug NP filtrate.

This sample of 78,500 ng total protein contained approximately 4.3 ng NP $PLA_2$ protein. By comparison, we use 500–2000 ng of highly purified $PLA_2$ to induce edema in this mouse model; and under these experimental conditions the maximal edema achieved is 160% of the contralateral paw minus 4–7% edema due to saline injection alone.

The data are expressed as percent of contralateral paw and as percent of maximal edema achieved with purified $PLA_2$. Fifty ul (78.5 ug) was injected into the paw 30 min. after the mice were treated with PX-13 in HEPES administered IP or by gavage at 30 or 60 mg/kg. After 3 hrs, the paws were excised and weighed.

|  | Percent Edema Inhibition | Percent of* Maximal | Percent |
|---|---|---|---|
| Saline Control | 106 ± 2.5 | — | — |
| NP-Homogenate alone | 124 ± 3.0 | 34% | — |
| PX-13: IP |  |  |  |
| 30 mg/kg | 120 ± 2.0 | 26% | 24% |
| 60 mg/kg | 115 ± 1.6 | 17% | 50% |
| PX-13: Gavage |  |  |  |
| 30 mg/kg | 122 ± 5.6 | — | — |
| 60 mg/kg | 118 ± 2.0 | 22% | 36% |

*calculated as previously described; $PLA_2$ alone = 160% edema − 106% control = 54% (maximal edema).

*calculated as previously described; $PLA_2$ alone=160% edema—106% control=54% (maximal edema). Considerable variability or overlap is noted in both 30 mg/kg PX samples; however, at 60 mg/kg both IP and gavage administration of PX-13 inhibited inflammation by 50% and 36%, respectively. These results indicate that nucleus pulposus extracts are inflammatory, and PX-13 protects against inflammation induced by nucleus pulposus extracts.

4. The lipid soluble (PX-13) and water soluble (PX-18) both inhibit the purified human disc type II, $PLA_2$ Both PX-13 and PX-18 inhibit the purified human disc type II, $PLA_2$. $PLA_2$ activity was measured as described in Franson et al., Prostaglandins, Leukotrienes and Essential Fatty Acids, 43:63–70, 1991, which is herein incorporated by reference in its entirety. The water soluble compound PX-18, displayed an $IC_{50}$ of 0.3 $\mu$M whereas the lipid soluble compound PX-13 displayed an $IC_{50}$ of 2.5 $\mu$M.

EXAMPLE 19

Ischemia-Reperfusion Injury

1. Small Bowel Transplantation: Ischemia-Reperfusion Injury

PX-13 and mepacrine inhibited $PLA_2$ activity in extracts of rat bowel, and PX-13 was a more effective inhibitor (by more than 2 log units) of $PLA_2$ enzymatic activity than mepacrine. Both compounds were shown to protect against ischemia and reperfusion injury following small bowel transplantation. These drugs reduced weight of the tissues after storage for 24 and 48 hours in the perfusate solution.

These drugs were also tested for their ability to enhance the preservation of tissues stored for subsequent transplantation. The small bowel was removed from rats, washed free of luminal contents and the tissue stored in University of Wisconsin (UW) preservative media±40 uM PX-13 or mepacrine for 48 hrs. The graft was then transplanted into rats with or without intravenous (IV) infusion of 20 mg/kg PX-13 or mepacrine at the time of transplantation. Upon transplantation, the bowel is immediately injured as evidenced by tissue darkening within two minutes. With PX-13 or mepacrine added to the media the gross and microscopic injury to tissue was dramatically reduced. Animals receiving PX-13 maintained normal bowel color in contrast to the blackening (necrosis) which occurs within minutes in the absence of drug. Treatment with the anti-malarial, anti-$PLA_2$ drug, mepacrine, produced some protection although not as great as with PX-13. Both PX-13 and mepacrine inhibit the peroxidation (malondialdehyde formation) of homogenized rat bowel, an indication that the membrane-stabilizing, $PLA_2$-inhibitors, also have anti-oxidant activity.

Recent studies completed in our laboratories demonstrate that ischemic bowel releases $PLA_2$ into the media in a time dependent manner. The addition of PX-13 reduced the enzyme release by more than 80% during 24 hrs of ischemia.

These results indicate that PX-13, which inhibits $PLA_2$ activity, exerts significant protective effects on tissues chosen for transplantation. PX-13 and related compounds may decrease complications resulting from tissue transplantation thereby increasing successful outcomes and reducing costs. The use of PX-13 and related compounds, acting as preservation-enhancing additives, may extend storage time and enhance the preservation of small bowel grafts and other tissue destined for transplantation in cold storage bathing solutions.

EXAMPLE 20

Parasitic Infection: protozoal parasites

1. Malaria: lipid soluble PX-13 inhibits in vitro replication of *Plasmodium falciparum*.

PX-13 was used to block the incorporation of $^3$H-hypoxanthine into the DNA, to provide a measure of growth, of *P.falciparum* cultures which were resistant to the drugs, chloroquine or mefloquine, which are normally used therapeutically. The growth of two strains in RBC cultures were tested:

The compound PX-13 inhibited the growth of clone W2 (*P.falciparum*), which is chloroquine resistant and mefloquine sensitive with an $IC_{50}$ of 13 ug/ml. This value for drug resistant clone W2 compares to control cultures sensitive to both drugs: $IC_{50}$ chloroquine=30 ng/ml vs mefloquine=1.3 ng/ml.

PX-13 also inhibited the growth of clone D6 (*P. falciparum*) which is chloroquine sensitive and mefloquine resistant, with an $IC_{50}$ of 17 ug/ml. This value for drug resistant clone D6 compares to control cultures sensitive to both drugs: $IC_{50}$ chloroquine=1.6 ng/ml; and mefloquine= 4.3 ng/ml.

PX-13 is active against strains of *P.falciparum* that are resistant to the drugs currently used for therapy. In addition, the slope of the inhibition curves indicates that PX-13 acts rapidly so that it can more rapidly interfere with the replication process or the disease in progress. These findings are also significant because the levels of current therapeutics necessary for control are often toxic. Recent findings indicate that the therapeutic index of PX-13 (dose for 50% lethality/dose for 50% effectiveness or $LD_{50}/ED_{50}$) is a large positive number, or highly favorable relative to the known toxicity problems for chloroquine, mefloquine, and other drugs used in the treatment of malaria.

2. Malaria: Water Soluble PX-18 inhibits in vitro replication of *Plasmodium falciparum*.

The water soluble compound PX-18 inhibited the same drug-resistant *P. falciparum* strains as described above. The $IC_{50}$ for PX-18 was 1.3 and 2.4 ug/ml. Thus, the water soluble PX-18 compound appears to be 10-times more effective than the lipid soluble compound PX-13.

The inhibitory effects of lipid soluble PX-13 and water soluble PX-18 on the growth of drug sensitive and drug resistant species of *Plasmodium falciparum* indicate that these PX compounds and possibly related PX compounds may be effective anti-parasitic drugs.

EXAMPLE 21
Preservation of Whole Blood

The effect of PX-13 and mepacrine on whole blood cell viability were tested as a function of time of storage. The results are summarized below.

|  | Percent Protection | | | |
| --- | --- | --- | --- | --- |
|  | LDH | | Hemoglobin | |
|  | 48 hr | 72 hr | 48 hr | 72 hr |
| A. Cells alone | 0 | 0 | 0 | 0 |
| B. Cells alone + PX-13 20 uM | 22 | 15 | 55 | 25 |
| C. Cells alone + PX-13 80 uM | 39 | 41 | 72 | 54 |
| D. Cells alone + PX-13 160 uM | 78 | 72 | 77 | 80 |
| E. Cells alone + mepacrine 20 uM | 58 | 27 | 61 | 45 |

Heparinized human blood was centrifuged at 400×g and the resulting plasma was removed and replaced with an equal volume of Dulbecco's medium. The resuspended cells were then incubated at 37° C. for 0–72 hrs. in a shaking water bath. At the indicated times, a 0.8 ml aliquot was removed and centrifuged at 400×g to sediment cells. Appearance of lactate dehydrogenase (LDH) and hemoglobin in the supernate was indicative of cell injury. PX-13 and mepacrine stabilized cells and decreased the injury as evidenced by diminished levels of LDH and hemoglobin in the supernate. This is expressed as percent protection.

The addition of snake venom $PLA_2$ accelerated the release of both LDH and hemoglobin at 24 hrs (not shown).

EXAMPLE 22
Blocking of thrombin-activated platelet aggregation.

Applicants previously demonstrated that a 25-$\mu$M dose of PX-13 inhibited platelet aggregation. Applicants have also observed that PX-13 inhibited serotonin release by thrombin-stimulated platelets. This observation supports the contention that the PX compounds of the present invention may block release of inflammatory mediators in the coagulation cascade. This observation also supports the use of PX compounds to inhibit thrombin-induced platelet aggregation and to act as anti-clotting agents.

EXAMPLE 23
Treatment for Snake Bite

Animal and human recipients of venomous snake bites require rapid treatment to alleviate the toxic inflammatory reactions which may be lethal. The compositions of the present invention are available in a readily injectable form for administration to the patient through intramuscular injection. The compositions of the present invention are stable for periods up to 3 months at room temperature.

Low molecular weight $PLA_2$ is a major toxic component of snake venoms. In venoms with neurotoxic effects (i.e. cobra venom), this is mediated by a $PLA_2$ which binds to a neuronal cells. Snake venom injuries have 3 components: 1) peripheral and central neurotoxicity (certain venoms), 2) systemic inflammation, including complement activation, and 3) extensive local tissue damage, including muscle necrosis and swelling which can cause distal vascular compromise (compartment syndrome). The following hypothetical example describes the treatment of a rattlesnake bite occurring several hours before conventional medical treatment with an emergency snakebite kit containing a water-soluble $PLA_2$ antagonist, PX-18, in injectable form.

A patient is bit by a rattlesnake on the upper calf while backpacking above the tree-line in Colorado. He uses his snake bite kit to attempt local suction extraction of venom at the bite site. He applies a tourniquet proximal to the bite. He then takes out the 2 ml syringe with 22 gauge needle, preloaded with 200 mg of PX-18 in sterile solution, which is contained in the kit. Following the kit instructions, he injects 1 ml of PX-18 intramuscularly (im) for systemic absorption, in the anterior thigh. He then injects the remaining 1 ml deep subcutaneously at the bite site, to attempt to neutralize the local concentration of venom $PLA_2$. After 30 minutes, he releases the tourniquet and proceeds to seek medical attention.

EXAMPLE 24
Reflex Sympathetic Dystrophy (RSD)

A patient presents with severe RSD characterized by persistent pain and limitation of movement at the wrist joint. Topical application of PX-13 to the wrist in a concentration of about 4% in the cream formulation described in Example 15 results in immediate pain relief and increased range of motion within 10 to 15 minutes.

Another patient presents with a two year history of RSD in the knee joint. This male patient previously received arthroscopic evaluations. This patient also had limited range of motion and became addicted to narcotics in an attempt to reduce pain. A combination of sympathetic blockade and cream containing PX-13 is topically applied and decreases the patient's report of pain and provides a full range of motion in the knee joint. The reduction in pain is immediate and the increased range of motion occurs within 10–20 minutes. This patient, who had been unemployed for an extended period, eliminated intake of narcotics and returned to work.

A third patient presented with RSD of the foot and ankle. This patient had no eversion or inversion of the foot. Topical application of PX-13 (about 4%) in a cream vehicle provides immediate and complete pain relief and restores full eversion and inversion within 20 minutes.

In each of the cases described above, pain relief analgesia is immediate with no production of anesthesia.

EXAMPLE 25
Acute Toxicity Studies

An $LD_{50}$ study was conducted to determine a lethal dose for PX-13 suspended in HEPES buffer at a pH of 7.4. A single IP dose of 50, 100, 200 or 400 mg/kg was administered to mice (n=6 per group). No deaths or gross physical or behavorial abnormalities were noted after 48 hours in all dosage groups. At 144 hrs one animal in the 400 mg/kg group died. No necropsy was performed. The scientist conducting this trial noted that "PX-13 was extremely well tolerated", confirming the results in the gut reperfusion experiments described in another example following IV administration of the test compound.

The results indicate that doses of 50 to 200 mg/kg administered IP to mice do not produce acute toxicity in terms of death or gross physical or behavorial abnormalities.

EXAMPLE 26
Effects of PX-18 on Histamine Release from Basophils

The protocol to evaluate the effects of PX-18 on histamine release is described below. Freshly drawn heparinized blood from donors non-medicated for 3 days is diluted 1:5 with PBS containing 1% human serum albumin (diluent). Test drugs are diluted in diluent to 10 times final concentration, and 25 $\mu$l per well is added to duplicate wells of round-bottomed microtiter plates. Generally 3-fold dilutions of drug, are examined four or five times. 200 $\mu$l of diluted blood is then added to each well. 5 minutes later, 25 $\mu$l of rabbit anti-human IgE (purchased from Dako) is added per well, to give final concentrations of 1/400 and 1/1200 of antibody. Unstimulated (background release wells) have 25 $\mu$l of diluent added. Plates are gently tapped for mixing, then incubated for 30 minutes. After incubation, plates are cooled on ice, spun down in a refrigerated centrifuge, and replaced on ice. 100 μl plasma is removed from each well for assay, and placed in a 1.5 ml Eppendorf tube containing acetylation reagent. Following acetylation, the histamine adduct is quantitated by a sensitive and specific commercial competitive assay, utilizing the competition of enzyme conjugated acetyl-histamine with sample analyte for binding to a specific antibody on the solid phase. A sample of blood is also lysed by repeated freeze/thaw to determine total blood histamine. Results are expressed as a percentage of total blood histamine release. In an acceptable assay maximal release is greater than 45% and background release is less than 15%. Experiments are performed in duplicate or triplicate using separate blood donors.

These experiments demonstrate that PX-18 inhibits the degranulation of basophils (and probably mast cells) in response to stimuli such as antibody surface-bound IgE. PX-18 is equipotent to epinephrine, a potent antianaphylactic drug, and more efficacious than cromolyn, a prototypic "mast-cell stabilizer". These results support the use of PX-18 and related compounds as compounds to treat allergic disease.

EXAMPLE 27
Effects of PX-18 on production of leukotrienes and prostaglandins by blood under basal and stimulated conditions The following protocol was employed to evaluate effects of PX-18 on production of leukotrienes and prostaglandins by blood cells under basal conditions, with ionophore stimulation of cyclooxygenase type I, and with lipopolysaccharide (LPS) induction of cyclooxygenase type II. Freshly-obtained heparinized blood from medication-free donors is diluted 1:1 with RPMI, and aliquoted in 0.6 ml amounts in sterile polypropylene 12×75 ml tubes. Test drugs are added at appropriate concentrations and diluted in saline with 1% human serum albumin. Control tubes have only diluent or drug vehicle added. Drugs are added five minutes prior to addition of stimulus, at 100×concentrations, (6 μl volumes). This is replicated for 3 racks of tubes, A thru C. A has no stimulus added, and has a 30 minute and 6 hr. tube for each drug concentration. B has 20 uM of the calcium ionophore A23187 added, and is incubated at 37° C. for 30 minutes. C has 5 ug/ml of E. coli strain Bort LPS added, and is incubated at 37° C. for 6 hours. At the end each time period, the appropriate tubes are placed on ice, centrifuged, and 0.4 ml of plasma carefully decanted into a tube containing formic acid and BHT to stop all reactions and preserve eicosanoid products. These tubes are then frozen at −70° C. for up to one week, then applied to Sep-pac mini columns and extracted into methanol. The methanol extract is aliquoted into 3 tubes and evaporated, then stored at −70° C. until the time of eicosanoid assay. Measurements include thromboxane (by a sensitive fluorometric plate-format assay) and either 15 HETE or LTB4 to measure lipoxygenase products.

The whole blood eicosanoid release experiments show that PX-18 appears to strongly inhibit the cytokine-inducible cyclooxygenase II, with less inhibition of the constitutive cyclooxygenase I enzyme, stimulated by ionophore, and even less or no inhibition of basal production of prostaglandins. This is an excellent anti-inflammatory profile as most NSAID-associated toxicities (i.e., gastric, renal, fluid retention, possibly asthma) are due to inhibition of constitutive cyclooxygenase I prostaglandin production, which plays a necessary physiologic role. cyclooxygenase II is involved in pathologic inflammation.

These studies also demonstrate that production of lipoxygenase products such as LTC4, is inhibited by PX-18. The comparison is to MK 592, a selective lipoxygenase inhibitor. PX-18 does not inhibit either the lipoxygenase or cycloxygenase enzymes, but rather PLA$_2$ which produces free arachidonic acid, thus depleting the pool of this enzyme substrate for the lipoxygenase and cyclooxygenase pathways. Our current experiments demonstrate that if exogenous arachidonic acid is added and lipoxygenase and cyclooxygenase metabolites are measured, the addition of PX-18, unlike indocin or MK 592 does not inhibit their production. These results support the notion that PX-18 inhibits PLA$_2$ and not downstream enzymes such as lipoxygenase and cyclooxygenase.

Additionally, blockade of secretory (s) PLA$_2$ activity decreases the production of lysophospholipid, the immediate and rate-limiting precursor for platelet-activating factor (PAF). Secretory PLA$_2$ as opposed to cytosolic perinuclear membrane-localized PLA$_2$, seems to be the key enzyme providing substrate which is acetylated to form PAF. PAF is a potent inflammatory mediator, a potent neutrophil chemotactic, and a key factor in tissue injury in such situations as ischemia. PAF is implicated in inflammatory diseases such as ulcerative colitis, and is unaffected by therapy with NSAIDs.

The invention has been described in detail with particular reference to certain embodiments, but variations and modifications can be made without departing from the spirit and the scope of the present invention as defined in the appended claims.

We claim:

1. A composition comprising:

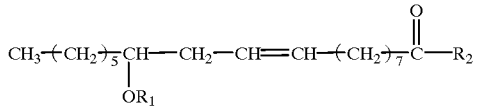

wherein R$_1$ is H, an alkyl group, an acyl group or an aliphatic group which may be functionalized or non-functionalized, which includes an acid group or salt thereof, and R$_2$ is an alkoxy group or an alkylamino group which includes a fatty moiety wherein a functionalized group has substituted for one or more hydrogens a double bond or one or more atoms or groups of atoms selected from the group consisting of C=C, OH, COOH, SO$_3$H, PO$_3$H, NH$_2$, O, and a halide, and a non-functionalized group has a maximum number of hydrogens per carbon atom.

2. The composition of claim 1, wherein R$_2$ is

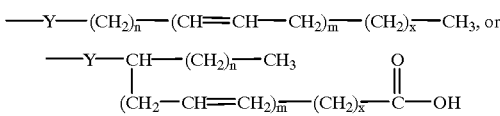

wherein n is an integer from 1 to 18, m is an integer from 1 to 4, x is an integer from 0 to 12, and Y is O, NH, or NR wherein R is an alkyl group of 1 to 6 carbon atoms, wherein the alkyl group of one to six atoms is functionalized or non-functionalized, wherein a functionalized alkyl group has substituted for one or more hydrogens a double bond or one or more atoms or groups of atoms selected from the group consisting of C=C, OH, COOH, SO$_3$H, PO$_3$H, NH$_2$, O, and a halide, and a non-functionalized alkyl group of 1 to 6 carbon atoms has a maximum number of hydrogens per carbon atom.

3. The composition of claim 1, wherein R$_1$ is a fatty moiety and R$_2$ is OH or an alkoxy group which is functionalized and includes another one of the fatty moieties wherein a functionalized alkoxy group has substituted for one or more hydrogens a double bond or one or more atoms or groups of atoms selected from the group consisting of C=C, OH, COOH, SO$_3$H, PO$_3$H, NH$_2$, O, and a halide.

4. The composition of claim 3, wherein $R_2$ is OH and $R_1$ is

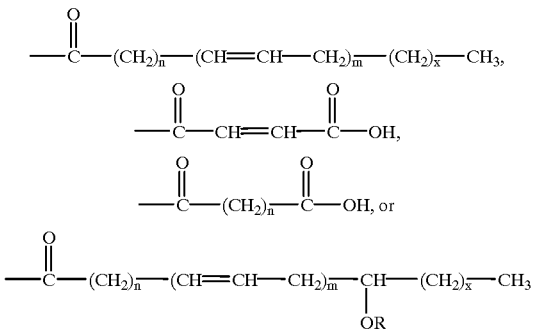

wherein n is an integer from 1 to 18, m is an integer from 1 to 4, x is an integer from 0 to 12, and R is H, a fatty moiety or an alkyl group which may be functionalized or non-functionalized, wherein a functionalized group has substituted for one or more hydrogens a double bond or one or more atoms or groups of atoms selected from the group consisting of C=C, OH, COOH, $SO_3H$, $PO_3H$, $NH_2$, O, and a halide, and a non-functionalized group has a maximum number of hydrogens per carbon atom.

5. A composition comprising:

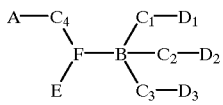

wherein A comprises H, OH, $NH_2$, or an acid or salt thereof;

B is selected from the group consisting of C, $(CH_2)_nC$, $N^+$, and $(CH_2)_n N^+$, wherein n is an integer from 1 to 24, and the $(CH_2)_n$ chain may be functionalized or non-functionalized;

$C_1$, $C_2$, $C_3$ and $C_4$ may be the same or different and are selected from the group consisting of $(CH_2)_n$ and $(CH_2-CH_2-O)y$, wherein n is an integer from 1 to 24, the $(CH_2)n$ chain may be functionalized or nonfunctionalized, and y is an integer from 1 to 12;

$D_1$, $D_2$ and $D_3$ are selected from the group consisting of fatty chains and H, wherein the fatty chains may be the same or different and are selected from the group consisting of fatty acid esters consisting of $CH_3(CH_2)_nCOO$ wherein n is an integer from 0 to 32, fatty acid amides consisting of $CH_3(CH_2)_nCONH$ wherein n is an integer from 0 to 32, and $(CH_2)_n$ wherein n is an integer from 1 to 32, wherein at least one of the fatty chains is unsaturated at one or more positions and the fatty chains may be of different lengths and may be unsaturated at different locations, wherein only $D_1$, $D_2$ or $D_3$ may be H;

E is H, $CO(CH_2)_nCH_3$ or $CO(CH_2)_nCOOH$ wherein n is an integer from 0 to 24 and the alkyl $(CH_2)_n$ chain may be functionalized or nonfunctionalized, or is the same as $A$-$C_4$; and F is selected from the group consisting of N, NR, P, P=O, CH and CR, wherein R is an alkyl chain of 1 to 6 carbons which may be functionalized or non-functionalized, wherein a functionalized $(CH_2)_n$ chain of 1 or more carbons has substituted for one or more hydrogens a double bond or one or more atoms or groups of atoms selected from the group consisting of C=C, OH, COOH, $SO_3H$, $PO_3H$, $NH_2$, O, and a halide, and a non-functionalized $(CH_2)_n$ chain has a maximum number of hydrogens per carbon atom.

6. The composition of claim 5, comprising:

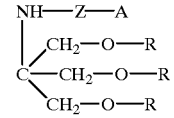

wherein the R groups may be different and each R is a fatty moiety of the formula

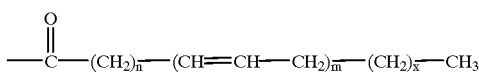

wherein n is an integer from 1 to 18, m is an integer from 1 to 4, x is an integer from 0 to 12, Z is a $C_1$ to $C_5$ aliphatic moiety which may be functionalized or non-functionalized, wherein a functionalized $C_1$ to $C_5$ aliphatic moiety has substituted for one or more hydrogens a double bond or one or more atoms or groups of atoms selected from the group consisting of C=C, OH, COOH, $SO_3H$, $PO_3H$, $NH_2$, O, and a halide, and a non-functionalized $C_1$ to $C_5$ aliphatic moiety has a maximum number of hydrogens per carbon atom, and A is COOH, $SO_3H$, $PO_3H$, an organic acid moiety, an organic acid radical, or salt form thereof.

7. The composition of claim 6, wherein A is selected from the group consisting of COOH, $SO_3H$ and $PO_3H$.

8. The composition of claim 5, comprising:

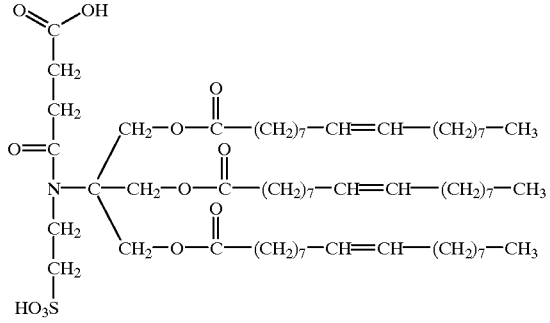

9. The composition of claim 5, comprising:

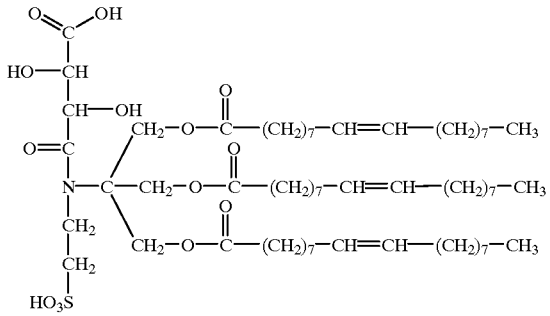

10. A composition comprising:

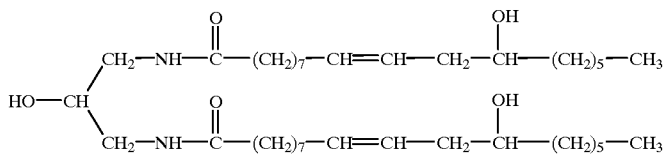

11. The composition of claim 5, wherein when any of the $(CH_2)_n$ chains is functionalized, and a functionalized $(CH_2)_n$ chain of 1 or more carbons has substituted for one or more hydrogens a double bond or one or more atoms or groups of atoms selected from the group consisting of C=C, OH, COOH, $SO_3H$, $PO_3H$, $NH_2$, O, and a halide.

12. The composition of claim 11, wherein $C_1$, $C_2$, $C_3$, and $C_4$ are independently functionalized or nonfunctionalized $(CH_2)_n$, and a nonfunctionalized $(CH_2)_n$ chain has a maximum number of hydrogens per carbon atom.

13. The composition of claim 12, wherein $C_4$ is functionalized.

14. The composition of claim 12, wherein $C_1$, $C_2$, or $C_3$ is functionalized and $D_1$, $D_2$, or $D_3$ is H.

15. The composition of claim 14, wherein A is an acid.

16. The composition of claim 15, comprising

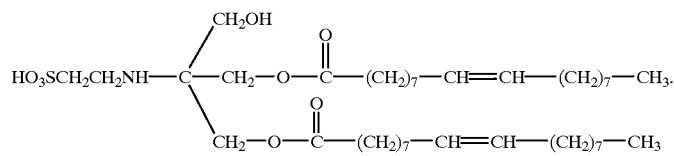

17. The composition of claim 15, comprising

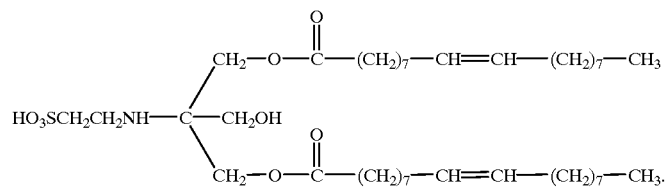

18. The composition of claim 15, comprising

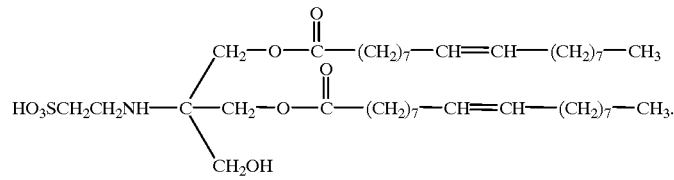

19. The composition of claim 11, wherein E is H or $CO(CH_2)_nCH_3$ and wherein the alkyl $(CH_2)_n$ chain is functionalized or nonfunctionalized, wherein a functionalized alkyl $(CH_2)_n$ chain of 1 or more carbons has substituted for one or more hydrogens a double bond or one or more atoms or groups of atoms selected from the group consisting of C=C, OH, COOH, $SO_3H$, $PO_3H$, $NH_2$, O, and a halide, and a non-functionalized alkyl $(CH_2)_n$ chain has a maximum number of hydrogens per carbon atom.

20. The composition of claim 19, wherein the alkyl $(CH_2)_n$ chain is functionalized.

21. The composition of claim 20, comprising

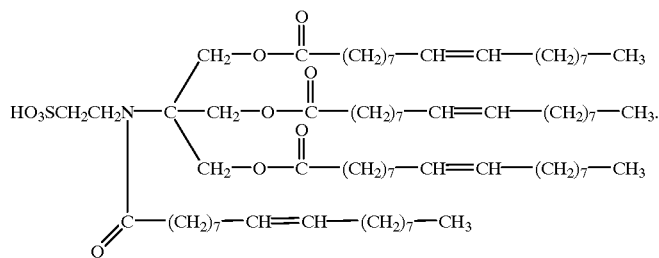

22. The composition of claim 20, wherein $C_1$, $C_2$, or $C_3$ is functionalized and $D_1$, $D_2$, or $D_3$ is H.
23. The composition of claim 22, wherein A is an acid.
24. The composition of claim 23, comprising

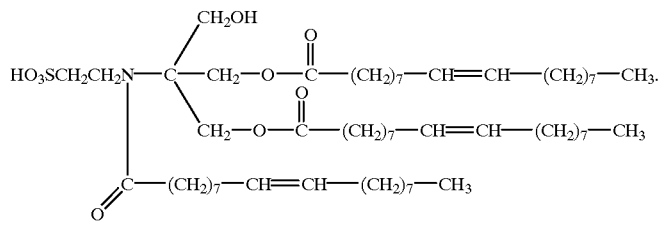

25. The composition of claim 23, comprising

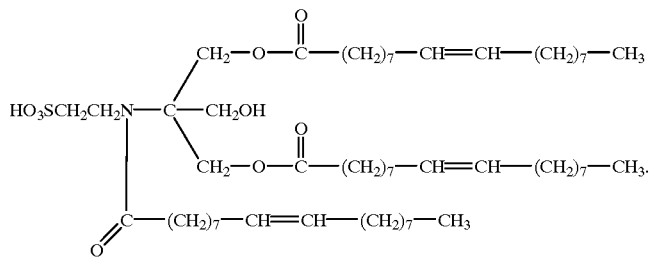

26. The composition of claim 23, comprising

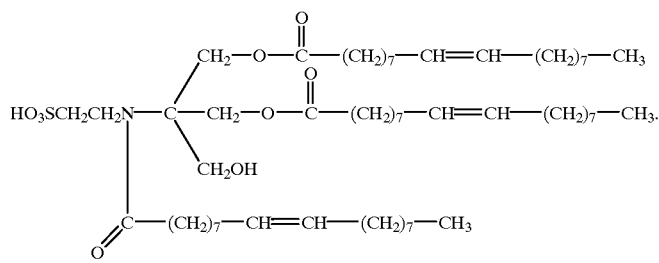

27. The composition of claim 5, wherein $D_1$, $D_2$ and $D_3$ each contain one or more unsaturated bonds.

28. The composition of claim 5, wherein $D_1$, $D_2$ and $D_3$ independently are fatty acid esters selected from the group consisting of oleic, linoleic, and arachidonic.

29. The composition of claim 5, wherein A is an acid.

30. The composition of claim 29, wherein the acid is selected from the group consisting of COOH, $SO_3H$, and $PO_3H$.

31. The composition of claim 5, wherein F is N or NR, wherein R is an alkyl chain of 1 to 6 carbons which may be functionalized or non-functionalized, wherein a functionalized alkyl $(CH_2)_n$ chain of 1 or more carbons has substituted for one or more hydrogens a double bond or one or more atoms or groups of atoms selected from the group consisting of C=C, OH, COOH, $SO_3H$, $PO_3H$, $NH_2$, O, and a halide, and a non-functionalized alkyl $(CH_2)_n$ chain has a maximum number of hydrogens per carbon atom.

* * * * *

UNITED STATES PATENT AND TRADEMARK OFFICE
CERTIFICATE OF CORRECTION

PATENT NO. : 6,020,510

DATED : February 1, 2000

INVENTOR(S) : Richard C. Franson, et al.

It is certified that error appears in the above-identified patent and that said Letters Patent is hereby corrected as shown below:

In the Claims:

Claim 3 should be amended to read:

3. A composition comprising:

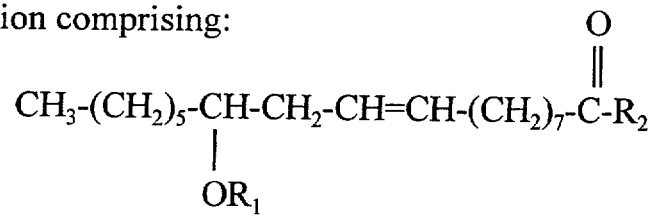

wherein $R_1$ is a fatty moiety and $R_2$ is OH or an alkoxy group which is functionalized and includes a fatty moiety wherein the functionalized alkoxy group has substituted for one or more hydrogens a double bond or one or more atoms or groups of atoms selected from the group consisting of C=C, OH, COOH, $SO_3H$, $PO_3H$, $NH_2.O$, and a halide.

Signed and Sealed this

Twenty-fifth Day of July, 2000

Attest:

Q. TODD DICKINSON

Attesting Officer

Director of Patents and Trademarks